United States Patent [19]

Champseix et al.

[11] Patent Number: 5,578,268
[45] Date of Patent: Nov. 26, 1996

[54] DEVICE FOR THE TRANSFER, AGITATION AND SAMPLING OF BLOOD PRODUCTS IN TUBES GROUPED IN CASSETTES

[75] Inventors: Henri Champseix, Montferrier/lez; Serge Champseix, Teyran, both of France

[73] Assignee: ABX, Montpellier, France

[21] Appl. No.: 351,298

[22] PCT Filed: Jun. 10, 1993

[86] PCT No.: PCT/FR93/00553

§ 371 Date: Dec. 9, 1994

§ 102(e) Date: Dec. 9, 1994

[87] PCT Pub. No.: WO93/25885

PCT Pub. Date: Dec. 23, 1993

[30] Foreign Application Priority Data

Jun. 11, 1992 [FR] France ................................. 92 07036

[51] Int. Cl.⁶ .................................................. G01N 35/10
[52] U.S. Cl. .............................. 422/63; 422/65; 422/100; 422/104; 436/43; 436/47; 436/54; 436/180; 141/130; 141/329; 366/211
[58] Field of Search ................................. 422/63, 65, 67, 422/81, 100, 103, 104; 54/43, 45, 47, 48, 49, 174, 180; 366/208, 209, 210, 211, 216; 141/130, 329

[56] References Cited

U.S. PATENT DOCUMENTS

| 4,609,017 | 9/1986 | Coulter et al. |
| 4,727,032 | 2/1988 | Baisch et al. |
| 4,861,553 | 4/1989 | Mawhirt et al. ........................... 422/65 |
| 4,911,897 | 3/1990 | Alphonse ................................. 422/270 |
| 5,217,694 | 6/1993 | Gibler et al. ............................. 422/104 |

FOREIGN PATENT DOCUMENTS

| 0061317 | 9/1982 | European Pat. Off. |
| 0263753 | 4/1988 | European Pat. Off. |

Primary Examiner—Jill Warden
Assistant Examiner—Long V. Le
Attorney, Agent, or Firm—Birch, Stewart, Kolasch & Birch, LLP

[57] ABSTRACT

A device for transferring, agitating, and sampling blood products sealed in tubes which are grouped together in cassettes wherein each cassette containing sample tubes is extracted from a storage receptacle by a moving loading and ejection carriage which shifts and positions it, using a retractable finger, in the cavity of a rotary carriage. The rotary carriage mixes the samples and stops so that sampling of tubes in the cassette can be performed by a sampling station which is movable in relation to the tubes temporarily immobilized in a vertical position with plugs facing downwards. The device is usable as a hematological analyzer.

29 Claims, 19 Drawing Sheets

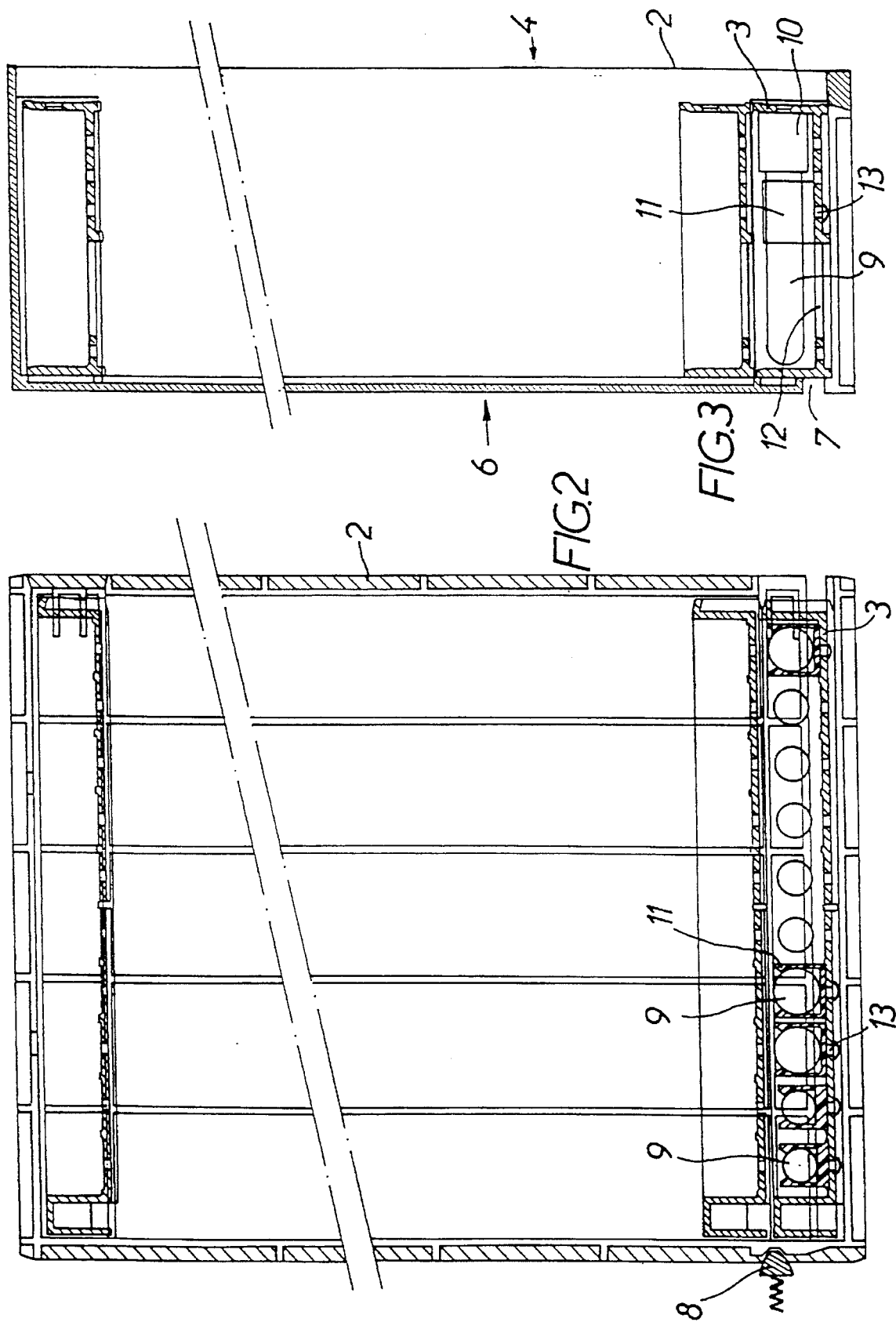

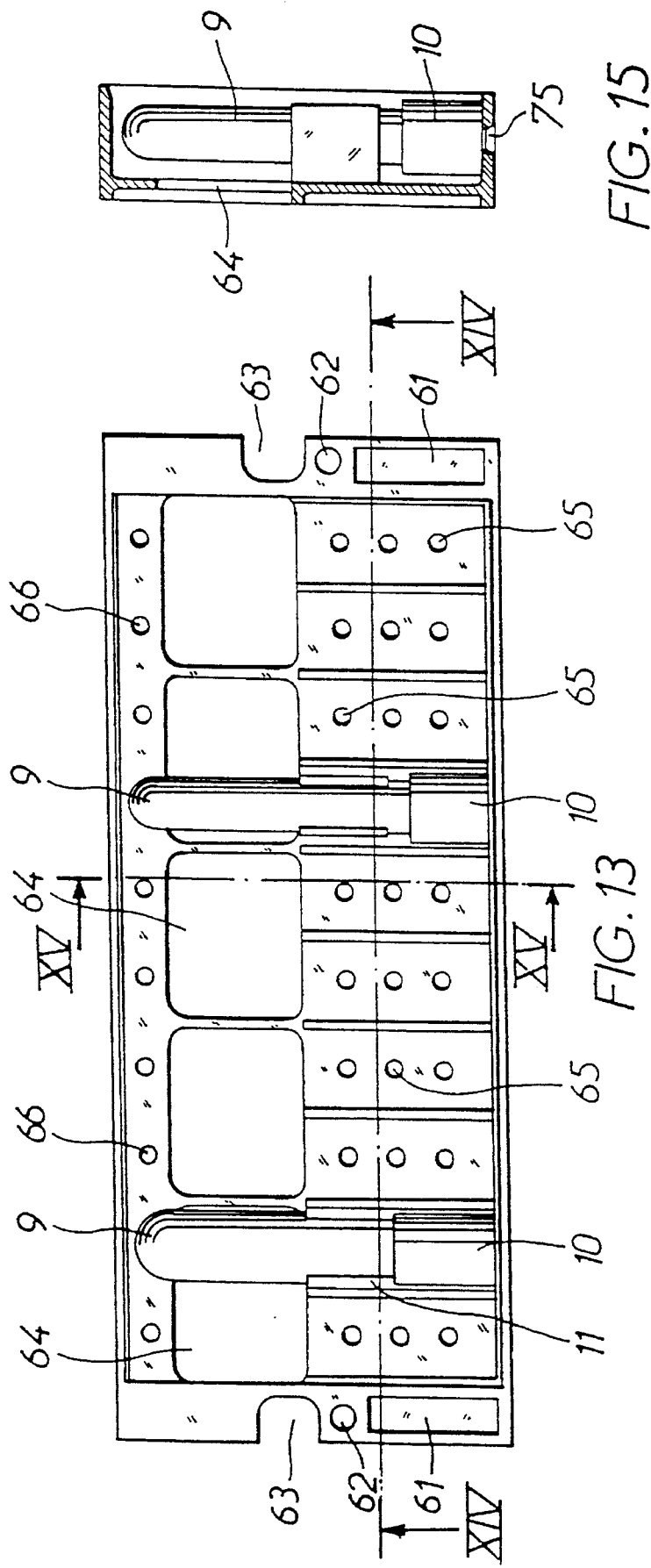

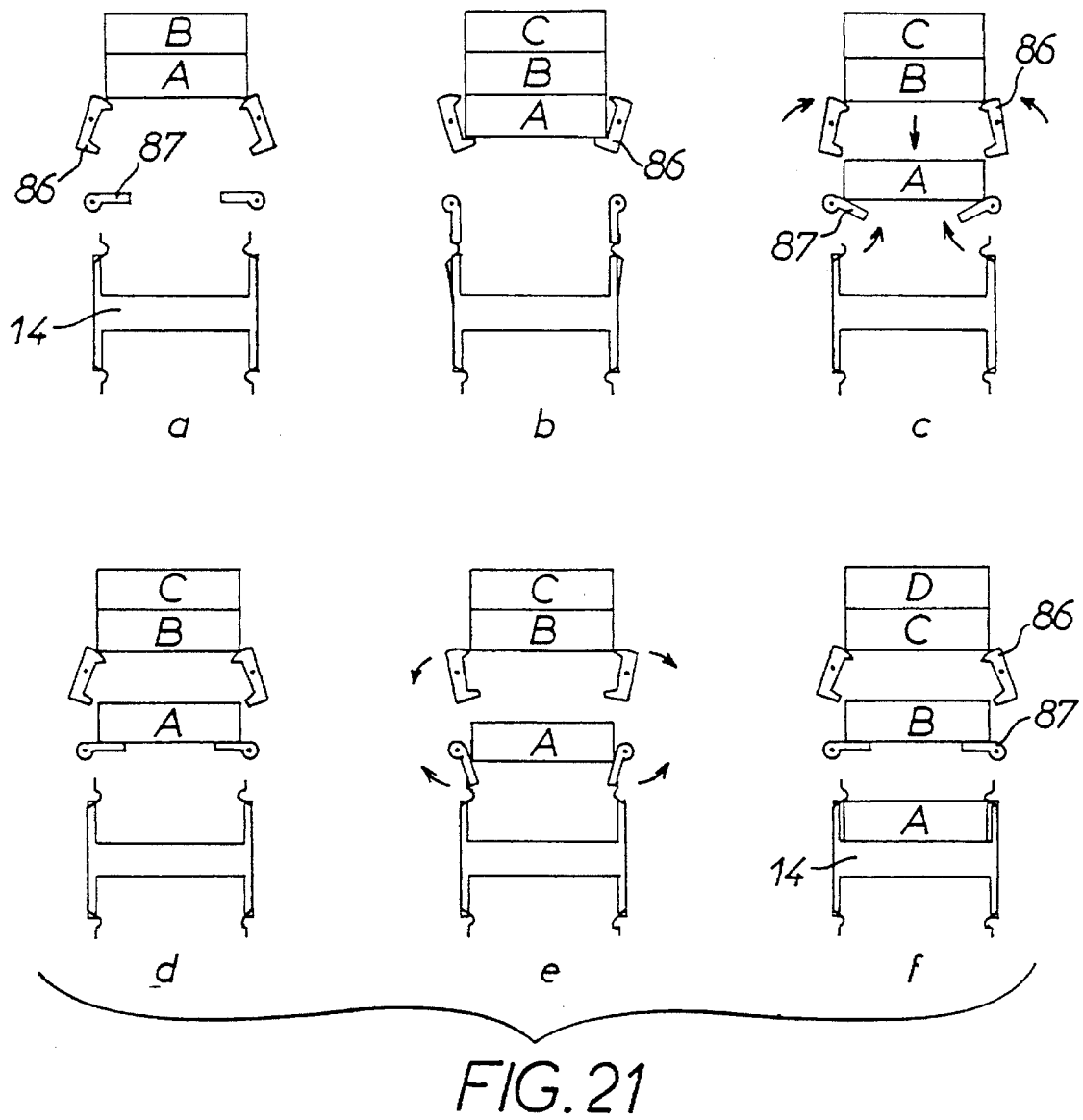
FIG. 21
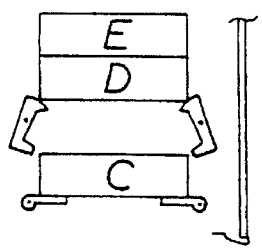
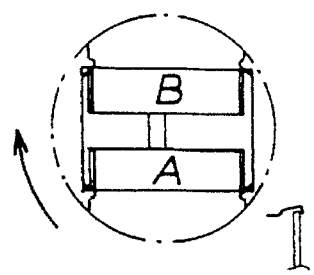
FIG. 22

5,578,268

DEVICE FOR THE TRANSFER, AGITATION AND SAMPLING OF BLOOD PRODUCTS IN TUBES GROUPED IN CASSETTES

BACKGROUND OF THE INVENTION

1. Field of the Invention

The invention relates to the field of analyzers used in haematology, in which blood samples are automatically analyzed, and it relates more particularly to a new device for transferring said samples, contained in closed receptacles and previously grouped together in cassettes, to the analyzer.

2. Description of the Related Art

It is known that, in order to analyze blood samples contained in sealed test tubes, it is necessary to move the test tubes to the analyzer, to agitate them to mix the blood, and then to pierce the bungs that close them in order to sample and transfer a small quantity of product to the analyzer. In order to avoid successive manipulations as much as possible, attempts have been made to automate all these operations. There is known, in particular, an automated process that consists in displacing cassettes of tubes of samples, with the help of a transport member, between an analyzer input area and an analyzer output area, a bung piercing station being provided between the two. For this purpose, the cassettes are received, one by one, on a combined pivoting table and conveyor belt. The table and conveyor belt unit pivots several times about its longitudinal axis so that the test tubes describe half-circles and their bungs move successively from a top position to a bottom position, this operation being continued until the sampled material is thoroughly mixed. Then, the transport member is halted for sufficient time to be able to carry out the piercing of the bungs and then feed the analyzer. This process, as described in EP-A-0159347, and the apparatus for implementing it, which forms a fully integrated and automated system containing a haematology type analyzer, do, however, have a certain number of drawbacks which are inherent in their design. For instance, in an input compartment of the apparatus, it is necessary, as a preliminary measure, to stack the cassettes filled with closed tubes of samples, one by one, manually. Furthermore, a lowering mechanism has to extract a cassette from the stack before it is taken over by the transport means, of the transfer belt type, in order to undergo subsequent agitation and displacement. This agitation, which is the result of inverting and not of complete rotation, has to be repeated several times, which delays the subsequent sampling operations. The pivoting table thus ensures the rearward tipping of the cassette before coming to a halt so that a first tube of sample can be partially moved out of a rack in order for a sample to be taken using a suction probe which has pierced the bung. This arrangement thus combines a number of mechanisms that do not permit sustained processing rates, or further sampling of a tube from which a sample has previously been taken.

SUMMARY OF THE INVENTION

With a view, in particular, to remedying these drawbacks, and, at the same time, to provide a modern device that improves the agitation process and permits higher processing rates, without halts during the loading or unloading stages, the Applicant has developed a completely different device.

A main object of the present invention is to provide a device for transferring, agitating and sampling blood products in tubes grouped together in cassettes, for use, in particular, with a haematology type analyzer in which the cassettes are transferred and positioned in a cavity in a rotary carriage which causes the samples to be mixed by rotation, and halts for the sampling of the tubes in the cassettes, which is carried out by a sampling station which can be moved past the tubes temporarily halted in vertical position, with the bungs facing downwards, a device in which each cassette, loaded with tubes of samples, is extracted from the storage receptacle by a mechanism that transfers it to an cavity in rotary carriage, said rotary carriage being provided with two U-shaped cradles symmetrical in relation to its rotational shaft, opening outwards, which cradles serve to hold and guide the cassettes and whereby a complementary mechanism causes the cassette to be ejected to a reception bin.

According to yet another main feature of the invention, the mechanism that causes a cassette to be displaced and positioned in a cavity of the rotary carriage, as well as the complementary mechanism that causes the cassette to be ejected towards the reception bin, are formed by a single loading and ejecting carriage which travels from the storage receptacle to the rotary carriage, and vice versa, sliding over a linear guide member, parallel to the shaft of the rotary carriage, and supports an ejection pin, fixed in relation thereto and orientated in the direction of the shaft of the rotary carriage. In addition, the loading and ejecting carriage supports a jack ensuring the operation of a retractable loading finger moving perpendicularly to the shaft of the rotary carriage. The ejection jack is mounted on a bracket integral with the loading and ejecting carriage.

According to yet another feature of the invention, the mechanism that ensures the positioning of a cassette in a cavity of the rotary carriage, by opening the clips, is formed by a plurality of retractable stops which are driven to tilt by the action of a motor, to retain the cassettes and to release them into the rotary carriage, step by step, through the effect of gravity.

Advantageously, a plurality of top stops are mounted at the same level on high pins, and a plurality of bottom stops are mounted, on a lower level on pins driven simultaneously in rotation and extending outwardly, respectively from two top and bottom pinions driven by the motor. The top stops are in the form of a catch symmetrical in relation to their pins, the tips of which face inwards, in the direction of the neighbouring top pin, while the bottom stops are asymmetrical in relation to their pins and face inwards in the direction of the neighbouring bottom pin.

According to an alternative embodiment, the mechanism that ensures the positioning of a cassette in a cavity in the rotary carriage is formed by two flaps and two pivoting members which are driven to tilt through the action of a single motor to retain the stack of cassettes and/or to release a cassette into the rotary carriage.

According another feature of the invention, the complementary mechanism for ejecting a cassette from the rotary carriage is formed by two ejectors sliding in a fixed guide block, the heads of which ejectors pass through openings in the rotary carriage to push the cassette out of the said carriage.

According to a particular feature of the invention, the sampling station can also reach a fixed support of a tube intended for priority sampling and, at the output of the apparatus, there is provided a pusher mechanism designed to push the cassettes into a collecting tray.

Other features and advantages of the invention will emerge from the following description, given by way of a non-limitative example of an embodiment of the device and its operation. However, it should be understood that the detailed description and specific examples, while indicating preferred embodiments of the invention, are given by way of illustration only, since various changes and modifications within the spirit and scope of the invention will become apparent to those skilled in the art from the detailed description.

BRIEF DESCRIPTION OF THE DRAWINGS

The present invention will become more fully understood from the detailed description given hereinbelow and the accompanying drawings, which are given by way of illustration only and thus are not limitative of the present invention, and wherein:

FIGS. 2 and 3 are respectively longitudinal and transverse vertical cross-sectional views of a tray of cassettes according to the present invention;

FIG. 13 is a plan view of a cassette of the present invention;

FIGS. 14 and 15 are cross-sectional views, respectively, along lines XIV—XIV and XV—XV of FIG. 13;

FIGS. 21 to 23 are schematic views of the mechanism with retractable stops and of the rotary carriage of the present invention during its loading-unloading stages;

DETAILED DESCRIPTION OF THE INVENTION

Figure 1:
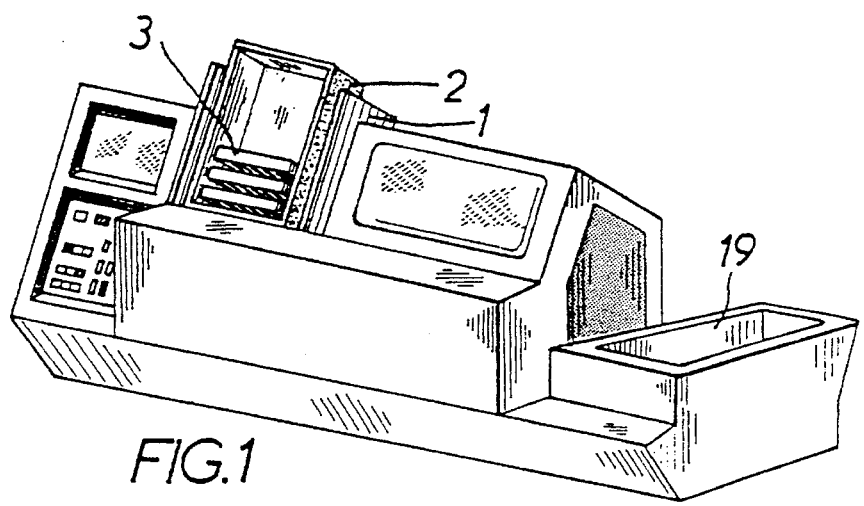
FIG. 1 is an overall view perspective view of a haematology type analyzer of the present invention.
Figure 4:
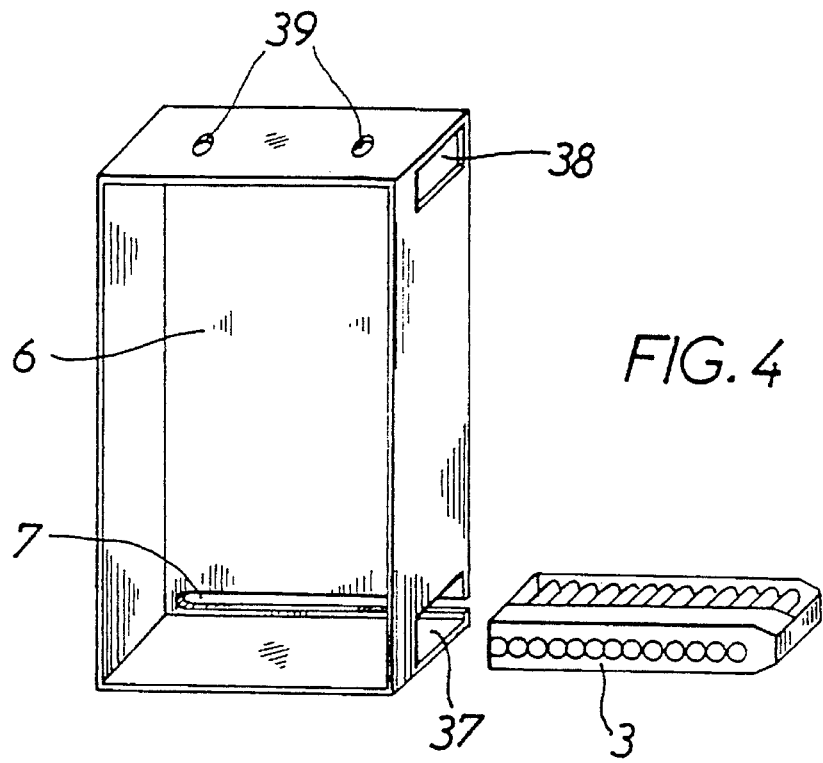
FIG. 4 is a perspective view of a tray of cassettes according to the present invention.

The haematology type analyzer represented in FIG. 1 is provided, towards one of its ends, with a cavity 1, opening upwards, which forms a receptacle into which can be placed a tray 2. The tray is filled, up to its full height, with cassettes 3, which are stacked on top of one another. It can be seen from FIGS. 2, 3 and 4 that a tray 2 takes the form of a parallelelopipedic box having an open front face 4 and a vertical rear face 6 having, at its lower portion, a transverse aperture 7 allowing passage of a member which will enable the cassette to be disengaged from the tray, as will be seen later. Tray 2, is pierced at the end of aperture 7, and in one of its side walls, by an opening 37 through which a cassette 3 can pass. Another, analogous, opening 38 is provided in the upper portion in the same side wall. Finally, in the horizontal wall forming the ceiling of the tray, there appear two ports 39 designed to allow the passage of pushers, as will become apparent in the course of the description. Each cassette 3 forms a flat receptacle in which are placed, side by side, several tubes 9 of sample closed by bungs 10. The tubes are held in place by clips 11, advantageously made of plastic and the wings of which are elastic, and which are fixed in a known manner, by a rivet 13 or another fixing means, to the bottom of the cassette. A longitudinal opening 12 is provided over the entire length of the bottom of the cassette to enable the tubes to be reached and disengaged from the clips. FIG. 2 shows that the tubes can be of different diameters. In addition, there is nothing to prevent the tubes from being of different lengths, the essential requirement being that their bungs should be aligned along an edge portion of the cassette.

Figure 5:
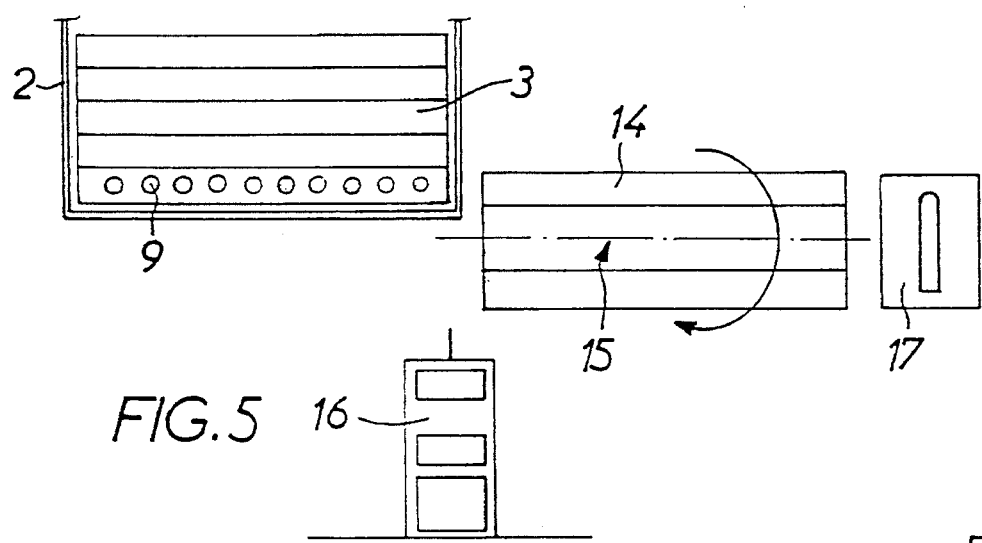
FIGS. 5 and 6 are schematic elevation and plan views, respectively, of the transfer device.
Figure 8:
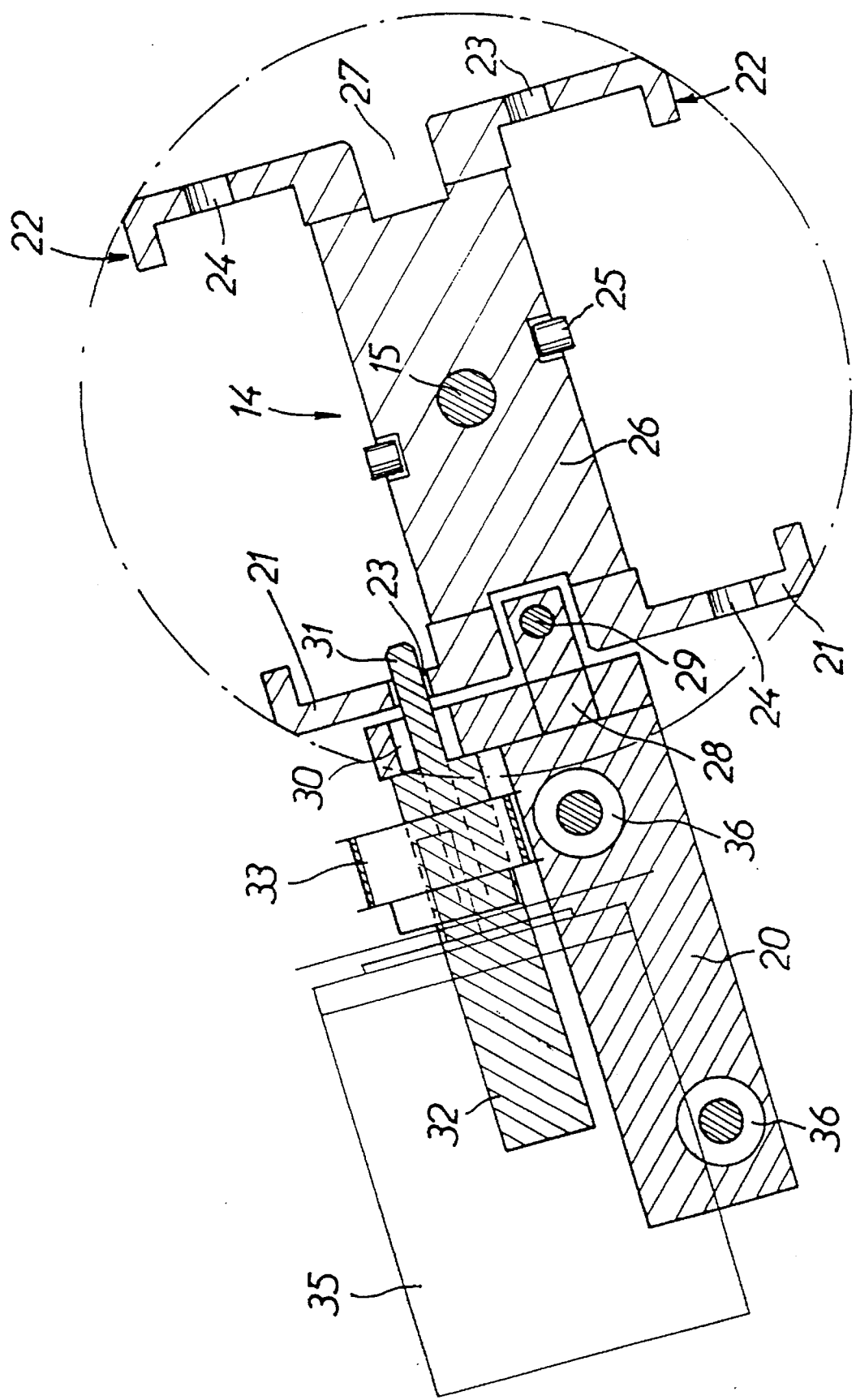
FIGS. 8 and 11 are larger-scale cross-sectional views of the loading and ejecting carriage and of the rotary carriage of the present invention, in loading position and in sampling position, respectively.

Inside the central portion of the analyzer of FIG. 1 is located the agitating and sampling mechanism, the flowsheets for which are shown in FIGS. 5 and 8. Beside receptacle 1 containing the tray 2 of cassettes 3 is disposed a rotary carriage 14 capable of rotating about its longitudinal shaft 15. It can be seen that the sample tubes 9 extend perpendicularly to said shaft 15. Below the rotary carriage 14 can move a sampling station 16 capable of halting beneath each of the tubes placed on the carriage. In the immediate vicinity of rotary carriage 14 is a fixed support 17 for a tube intended for priority sampling.

Station 16, also referred to as a mobile piercing device, is described with reference to FIG. 7. It contains a base 40 capable of sliding along rods 41 through the action of a rotary screw 42 driven by a motor 43 through the intermediary of a serrated belt 44 and of a drive pulley 45.

From the base 40 rise guide columns 46 on which slides a plate 47 bearing a vertical sampling needle 48, with its tip facing upwards. Plate 47 is moved upwards through the action of a jack 49 causing panels 50 articulated on a pin 51 to pivot. Base 40 further carries another needle 52 designed for micro-sampling, the tip of this needle facing downwards. A sampling valve 53 is used to collect and distribute the blood sampled by one or the other of the needles.

At the output of the apparatus, (see FIG. 6), beyond fixed support 17, there is provided a pusher which enables a cassette to be displaced laterally in the direction of a collecting tray 2 placed flat in a reception bin 19 (FIG. 1). The ports 39, mentioned earlier, serve to allow passage of the rods of said pusher.

Figure 6:
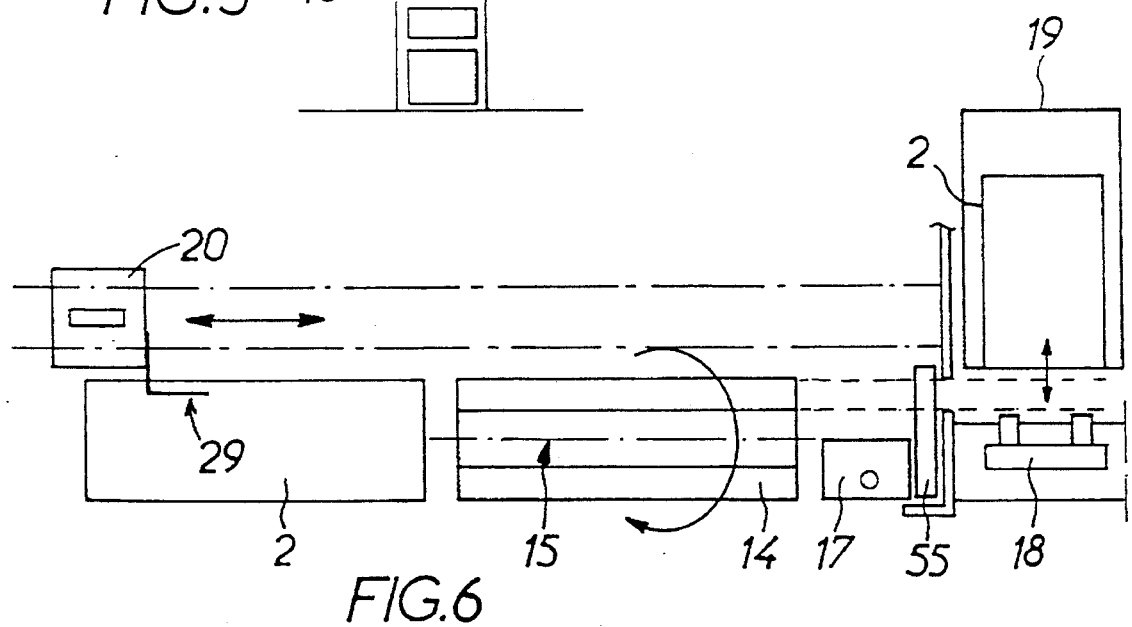

FIG. 6 shows that, parallel to shaft 15, but in a vertical plane different from that of the tray and the rotary carriage, moves a loading and ejecting carriage 20, the function of which is to disengage the cassettes from tray 2 and to place them on rotary carriage 14, and to disengage them from said rotary carriage and place them in the collecting tray.

Figure 9:
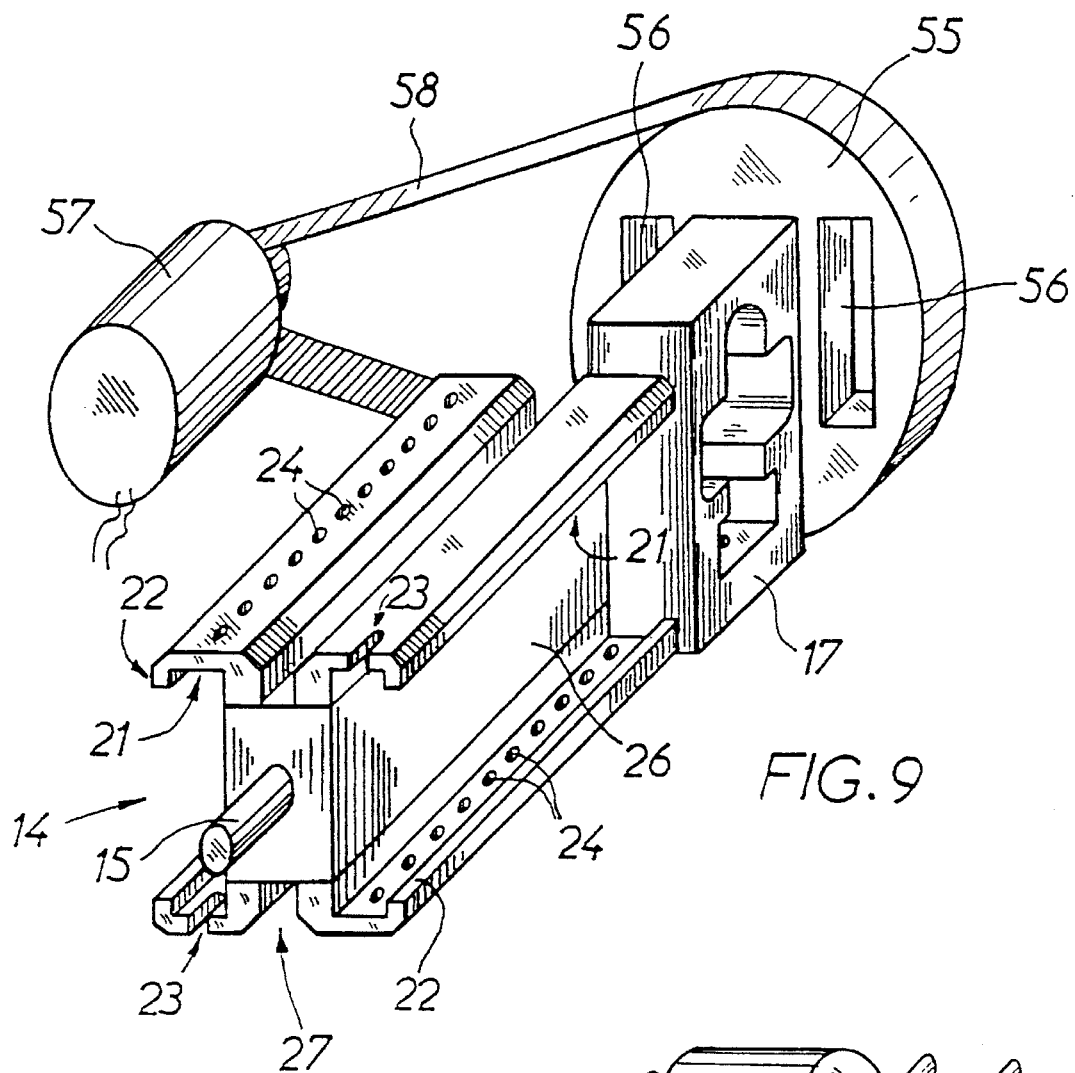
FIGS. 9 and 10 are perspective views, respectively, of the rotary carriage and of the loading and ejecting carriage of the present invention.
Figure 11:
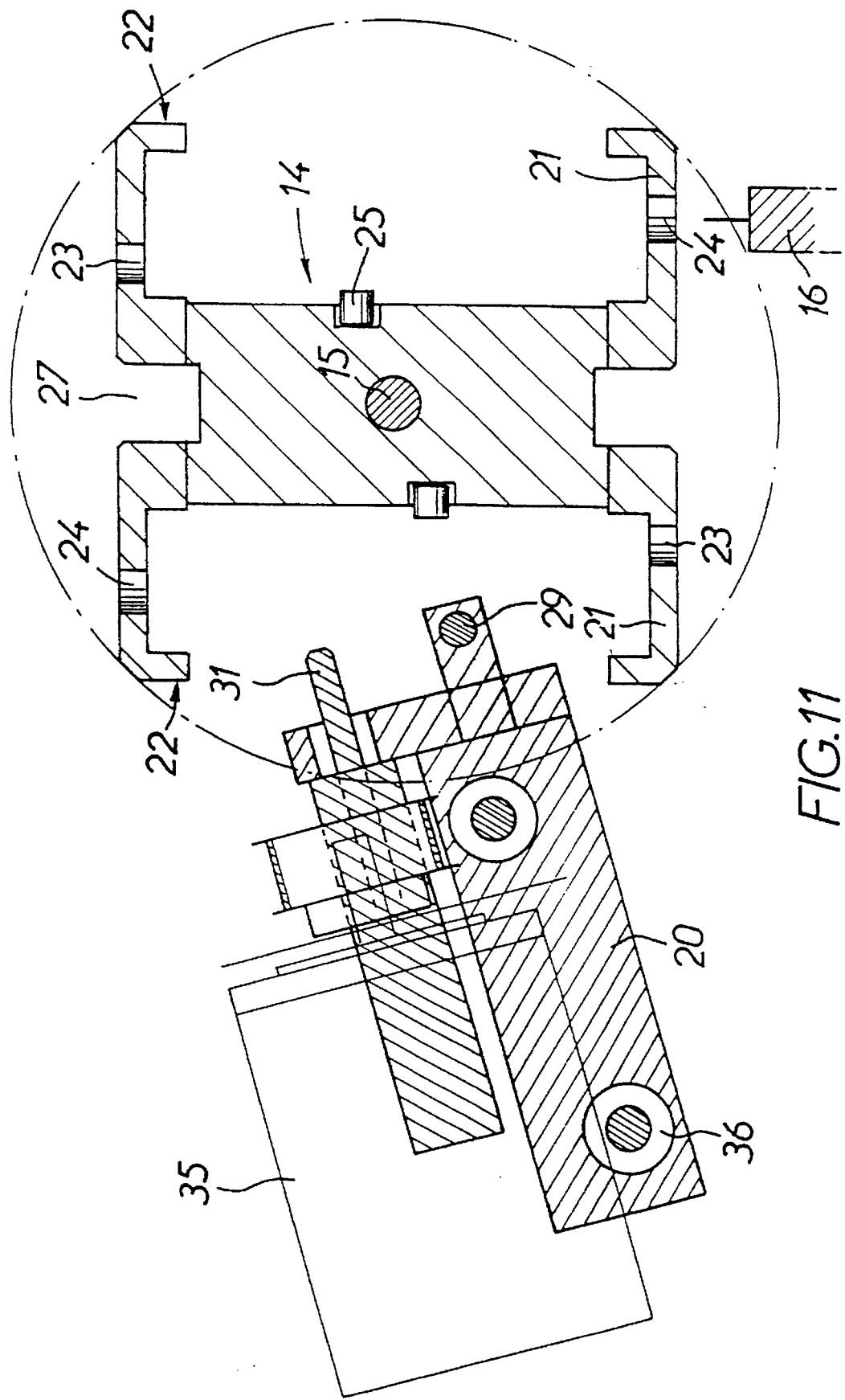

FIGS. 8, 9 and 11 illustrate in greater detail the assembly of carriage 20 in relation to rotary carriage 14. The latter is provided with two U-shaped cradles 21, symmetrical in relation to shaft 15, opening outwards and framing a central body 26 of a parallelopipedic shape. Cradles 21, each designed to receive a cassette, are extended by small rims 22 bending back over the cradles and serving to hold and guide the cassettes. One of the sides of the cradle opens, at one of its ends, in a slot 23, and the other side is pierced by a plurality of ports 24 corresponding to the number of tubes in a cassette. The central body 26, at the bottom of the cradles, is cut away to receive a cassette locking clip 25. Finally, a disengagement groove 27 is provided on either end of the central body, between the cradles, symmetrically in relation to shaft 15.

We have seen that rotary carriage 14 was mounted on a shaft 15. The latter extends beyond the carriage behind support 17 as far as a drive pulley 55 which can be seen in FIG. 9. This pulley has a diameter at least equal to the circle described by the rotary carriage, the circumference of which is marked, in particular, in FIG. 8. Pulley 55 is pierced by two rectangular openings 56 designed to permit the passage of the cassettes in the ejection stage. The pulley is driven in rotation by a motor 57 through the intermediary of a serrated belt 58.

Figure 10:
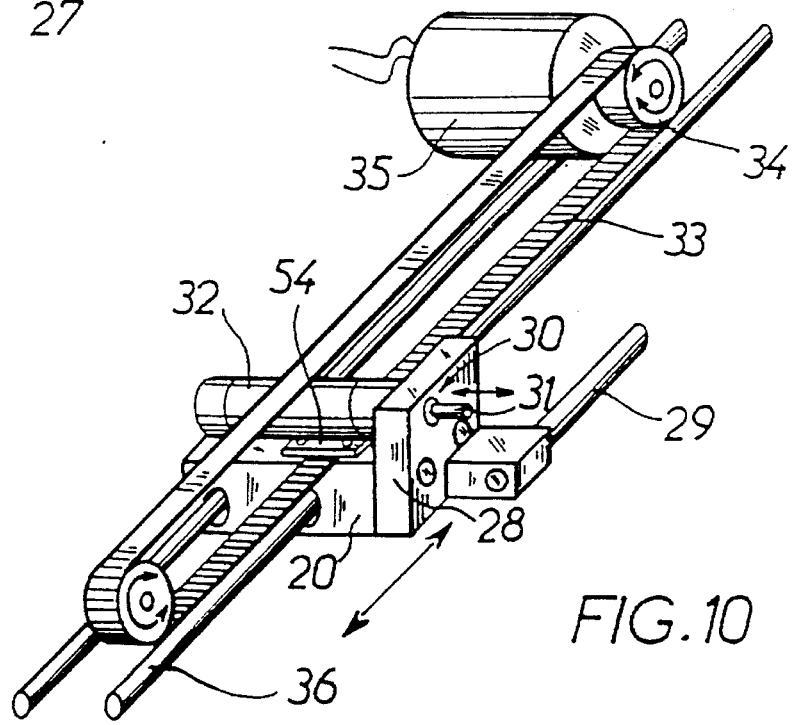

The loading carriage 20, which can be seen in FIGS. 8, 10 and 11 ends, in the vicinity of the rotary carriage 14, in a bracket 28 which supports an ejection pin 29 fixed in relation to the carriage, extending in the direction of shaft 15, as can also be seen in FIG. 6. The bracket is further pierced by a port 30 to allow through a retractable loading finger 31 constituted by the mobile rod of a jack 32 borne by the said carriage. The finger is displaced perpendicularly to the shaft 15 of the rotary carriage 14. The movement of the carriage 20 is ensured by an endless notched belt 33, the lower run of which is fixed by means of a small plate 54 to the upper face of the carriage. The notched belt is driven by a drive pulley 34, itself connected to a motor 35. Carriage 20 is thus capable of moving from tray 2 to rotary carriage 14, and to pulley 55, and vice versa, by sliding along the rods of ball bearing-mounted guides 36, parallel to the shaft 15 of the rotary carriage.

In FIG. 8, rotary carriage 14 is in loading position. With reference also to FIGS. 5 and 8, the operation of the device will now be described. Carriage 20 has the function of disengaging bottom cassette 3 from tray 2. As we have seen, the tray is designed to permit this disengagement. Motor 35 drives serrated belt 33, which will cause carriage 20 to slide along the rods of the ball bearing-mounted guides 36, that is to say rearwards in FIG. 8, or from left to right in FIG. 6. Pin 29 will thus be displaced parallel to shaft 15, travelling inside disengagement groove 27 provided for this purpose. On the other hand, during this movement, it is retractable finger 31 that will push the cassette, extract it from the tray and place it in the top cradle, 21, engaging at the end of the stroke in the corresponding notch 23; then it retracts. Carriage 20 can then return to its starting position and release rotary carriage 14, which will rotate 180° under the action of pulley 55 to place the bottom cradle in top position this time, and present it so that the second cassette can be loaded, in accordance with the above process. The loading carriage returns once again to its starting position, and the rotary carriage performs a certain number of rotations to agitate the tubes; then it halts in vertical position, as shown in FIG. 11. The sampling station 16, which can be seen in FIGS. 5 and 7, will then move beneath the cassette at a halt in the upper cradle 21 of the rotary carriage. The tubes carried by the cassette, thus halted, are in a vertical position, with the bungs facing downwards. The product in the first tube is then sampled. When this sampling operation is completed, station 16 returns to its starting point, which allows further agitation by rotation of the carriage. During this time, the product sampled in the first tube is analyzed. Then, the station is placed, after the carriage has been halted again, beneath the second tube of the cassette, etc. When the last tube has been sampled, it is obviously the cassette in the other cradle that will be halted in vertical position, so as to be sampled in its turn. The sampled cassette, which is thus located beside the loading carriage, can now be ejected. For this purpose, finger 31 retracts to allow carriage 20 to travel once again in the direction of rotary carriage 14 without driving the following cassette 3 of tray 2, until pin 29 engages the side of the empty cassette halted in its cradle and disengages it from the rotary carriage. It can be seen from FIG. 6 that carriage 20 can travel beyond the said rotary carriage and push the empty cassette beyond fixed support 17. The cassette will then pass through halted pulley 55 via an opening 56 (FIG. 9) before being acted upon by the pusher mechanism 18 which will disengage it into the tray 2 placed flat on the collecting surface 19.

The empty cassettes will again be stacked in this collecting tray, from which they can be extracted one by one, if necessary. The entire contents of the tray can thus be recovered easily.

We have seen that, in front of the empty cassette collecting station, there is located a fixed support 17 for a tube of sample.

This station is used to carry out a priority sampling or a micro-sampling operation. There is, indeed, nothing to prevent mobile sampling station 18 from being manually withdrawn, momentarily, from the area of rotary carriage 14. This special sampling operation is made possible thanks to the mobility of the sampling station, which can be displaced in relation to the fixed station. In addition, this operation is effected without opening the tube, and without any risk of contamination, and it allows the bar code on the tube to be read on a priority basis, the bar code being displaced with the sampling station.

For priority sampling of a tube placed in support 17, it is the needle 48 of the mobile piercing device which, in an ascending movement, will pass through an orifice in the said support to reach the closed tube placed in inverted position.

For micro-sampling, a tube is presented manually to fixed needle 52.

The device described previously offers the possibility of taking two or more samples, or a fresh sample, from a tube already sampled previously, since the station is capable of reversing. Furthermore, the sampling rates are higher than in the case of known equipment, as it is possible for the cassettes to be unloaded during these sampling operations, whence savings in terms of time and personnel.

Figure 12:
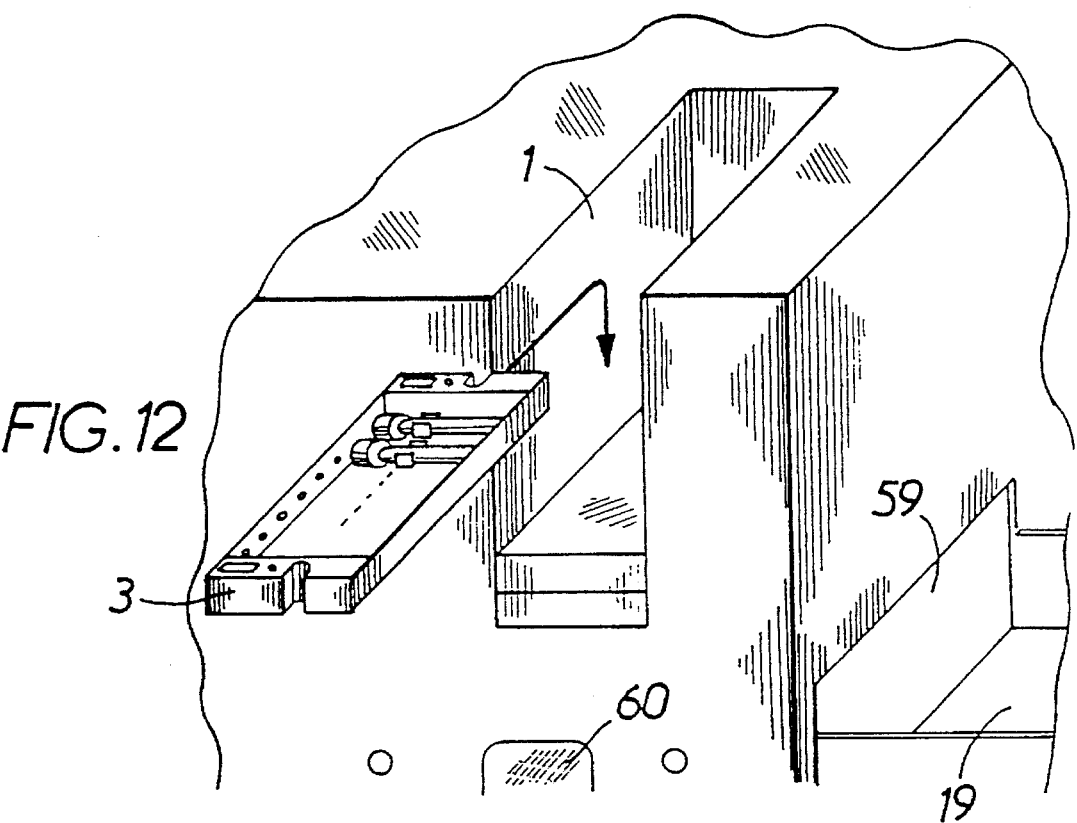
FIG. 12 is a partial perspective view of the front of the haematology type analyzer according to an alterative embodiment of the present invention.

FIGS. 12 to 23 show another alternative embodiment of a sample transferring device according to the invention. The haematology type analyzer has substantially the same configuration as that illustrated in FIG. 1. However, the cassettes 3 are no longer placed in a tray; they are stacked one on top of the other directly in cavity 1 of the analyzer. FIG. 12 schematically represents the front portion of the analyzer. Cavity 1, in this variant, is located above the central portion of the analyzer containing the rotary carriage. On the side is located the reception bin 19, which communicates with the central portion via an opening 59. The front face of the analyzer is provided with a window 60 permitting the passage of the micro-sampling needle.

Cassette 3 used in this variant is represented in FIGS. 13, 14 and 15. The cassette described with reference to FIGS. 2 and 3 could also be used. At each of its ends, it has a rectangular portion that is depressed in relation to its neighbouring surface to accommodate a label 61, a hole 62 to permit the passage of ejectors and a central cut away portion 63. The sample tubes 9 closed by bungs 10 are held by clips 11. It will be noted, in particular, in FIGS. 13 and 15 that openings 64 are provided to enable the tubes to be withdrawn from the cassette. The small holes 65 seen in FIG. 13 serve to fix the clips to the cassette, and the row of small holes 66 aligned along one edge portion is provided for the purpose of holding packing means (not show ) for use with shorter tubes. Finally, FIG. 15 shows that orifices 75 are provided at the base of the cassette, opposite each tube to permit the passage of the sampling needle.

Figure 16:
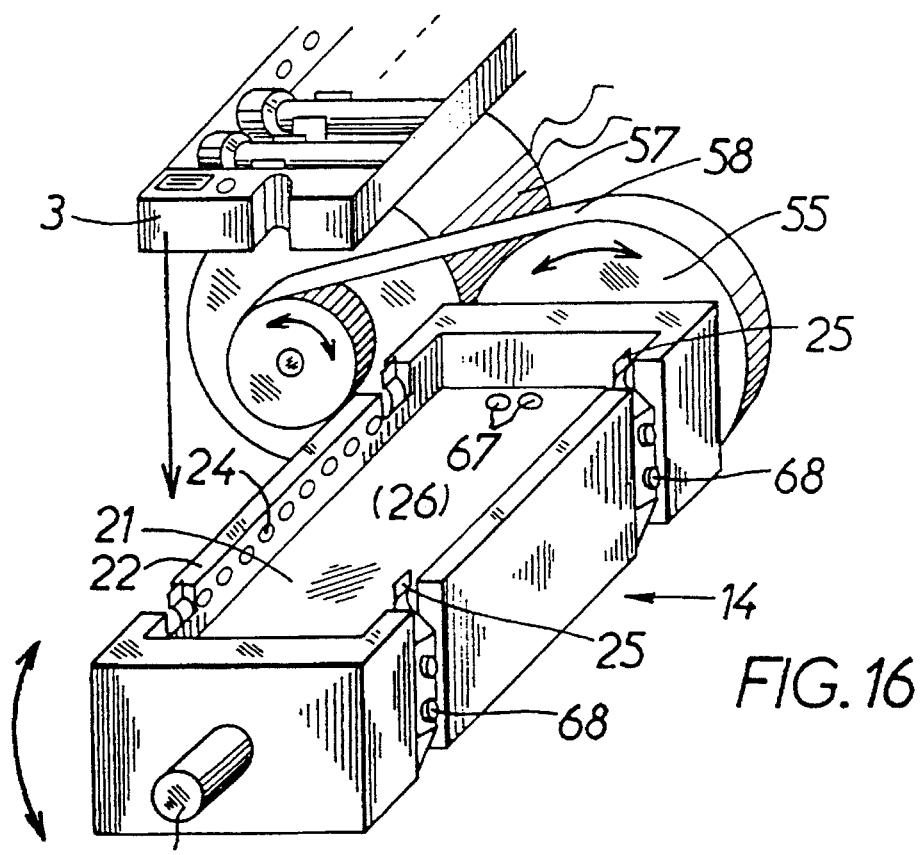
FIG. 16 is a perspective view of an alternative embodiment of the rotary carriage of the present invention.

Rotary carriage 14, according to this variant, illustrated in FIG. 16, also has two U-shaped cradles symmetrical in relation to its rotational shaft 15. The rims 22 are pierced by orifices 24 corresponding to the tubes of the cassette. It will be noted that there are, at each end of the cradles, clips 25 serving to hold the cassette in place on the carriage, the said clips being fixed by screws 68. The central body 26 is further pierced by openings 67 to permit the passage of the ejectors. Shaft 15 projects from rotary carriage 14 up to drive pulley 55 connected to motor 57 by serrated belt 58. It can be seen from this figure that rotary carriage 14 is in a horizontal position, that is to say that one of the two cradles 21 opens upwards and is ready to receive a cassette 3 from the cavity of the analyzer, placed just above it, as previously indicated.

Figure 17:
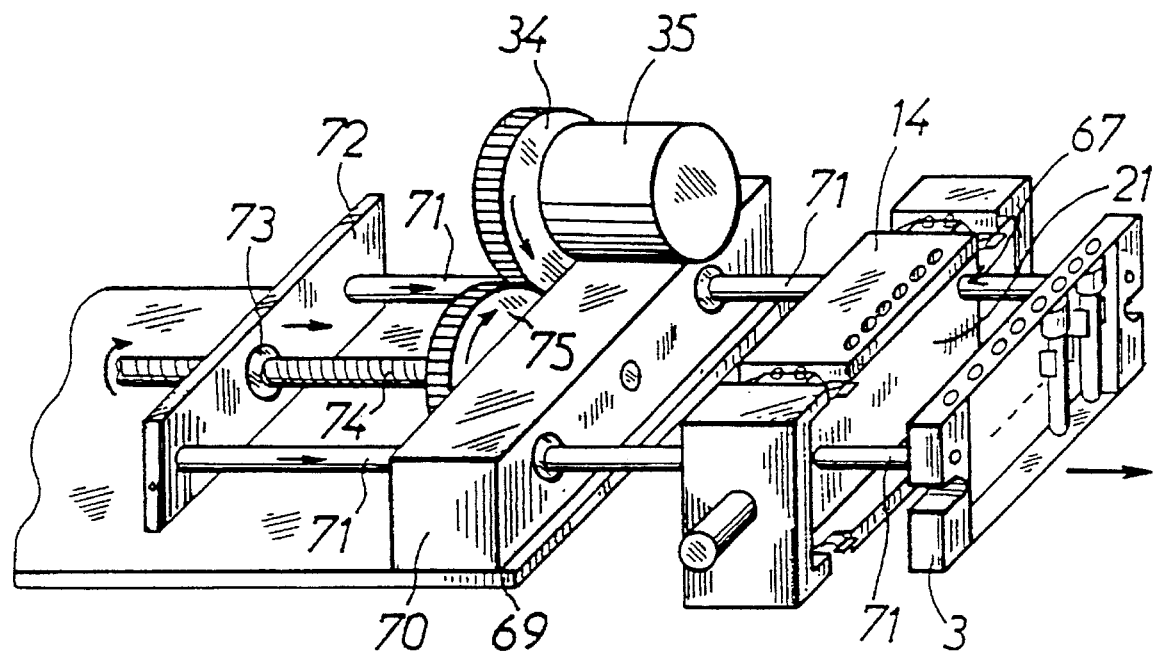
FIG. 17 is a perspective view of an alternative embodiment of the ejection mechanism of the present invention.
Figure 18:
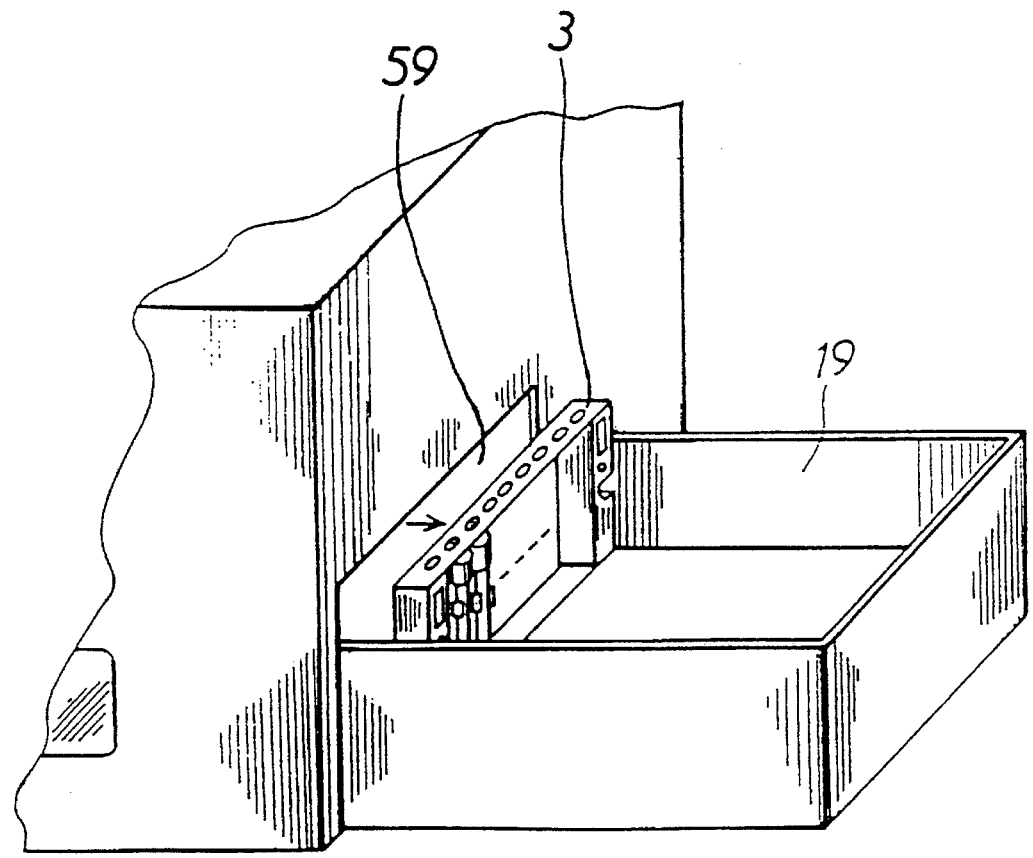
FIG. 18 is a partial perspective view of the reception bin of the haematology type analyzer according to an alternative embodiment of the present invention.

The mechanism that enables a cassette 3 to be ejected from rotary carriage 14 is represented in FIG. 17. On a fixed support plate 69 is fixed a guide block 70 for two sliding ejectors 71. The latter are connected at their ends to one and the same plate 72, which is capable of moving over the plate 69. For this purpose, the plate is equipped with a nut 73 cooperating with a rotating screw 74, the latter being driven by pinion 34 of a motor 35 integral with the guide block, via a pinion 75 mounted on the end of screw 74. Rotary carriage 14 is here in the ejection position, that is to say it has swung 90° in relation to the position illustrated in FIG. 16. The cradles 21 are orientated vertically. A cassette 3 can be seen being ejected (towards the right in the figure) by the heads of the ejectors 71 which have passed through the openings 63 of the other cassette and the openings 67 of the rotary carriage to push the cassette out of the said carriage. FIG. 18 shows that the cassette in question is thus supplied to the reception bin 19 after passing through opening 59.

Figure 19:
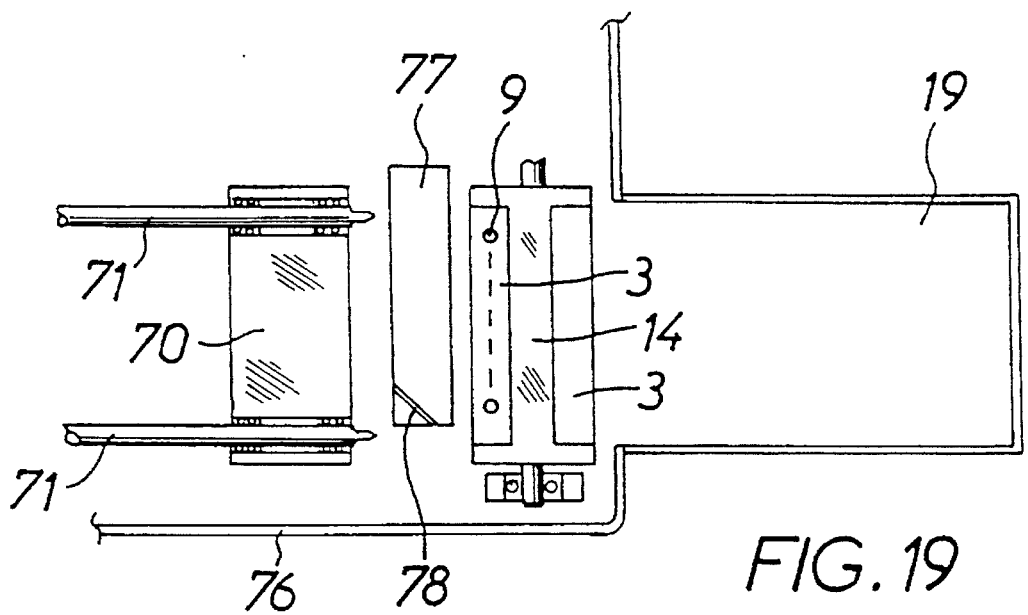
FIG. 19 is a schematic plan view of the elements of the variant of the transfer device of the present invention.

FIG. 19 schematically represents the layout of the essential mechanisms housed inside the cover 76 of the analyzer, at the end of which can be seen reception bin 19. In the left-hand portion are located the plate and the guide block 70 which support the sliding ejectors 71. Beside them is placed a reading assembly 77 of the bar code type, which is displaceable with the sampling station or the mobile piercing device of the type described with reference to the first variant.

The assembly in question is located in the immediate vicinity of the rotary carriage 14, shown here in sampling position. A tube 9 is shown in the vertical position, the tube being in the process of being pierced, and being read via the bar code in cassette 3, which can be seen to the left of the carriage. A mirror 78 provided on assembly 77 is used to enable the bar codes on tube 9 to be read successively. The other cavity in the carriage also contains a cassette 3 stored for pre-agitation.

As seen previously, rotary carriage 14 is disposed under cavity 1 of the analyzer and receives the cassettes by gravity feed. To ensure the loading of the said carriage, a mechanism is used, generally designated by reference number 90, which brings into play a set of retractable stops illustrated in FIG. 20. A single drive motor 79 drives, via a drive pinion 80 and a reversing pinion 81, two top pinions 82, which themselves act on two bottom pinions 83. Top pins 84 and bottom pins 85 of the said pinions, extending outwards, each carry respectively two top stops 86 and two bottom stops 87. It can be seen that the top stops 86 take the form of a catch symmetrical in relation to pin 84, the tips 88 of the top stops 86 being orientated inwards in the direction of the adjacent top pin. On the other hand, bottom stops 87 are asymmetrical, but they are also inwardly orientated. The top and bottom stops can thus be tilted by the action of single motor 79.

The said system with retractable stops is located at the base of cavity 1 and above the rotary carriage. Its function is to retain and distribute the cassettes one by one into the carriage. The four top stops 86 can support a cassette with the tops of their upper tips or with their lower tips, depending on whether the top stops are inclined, in relation to the vertical, towards the area internal or external to pins 84.

Figure 20:
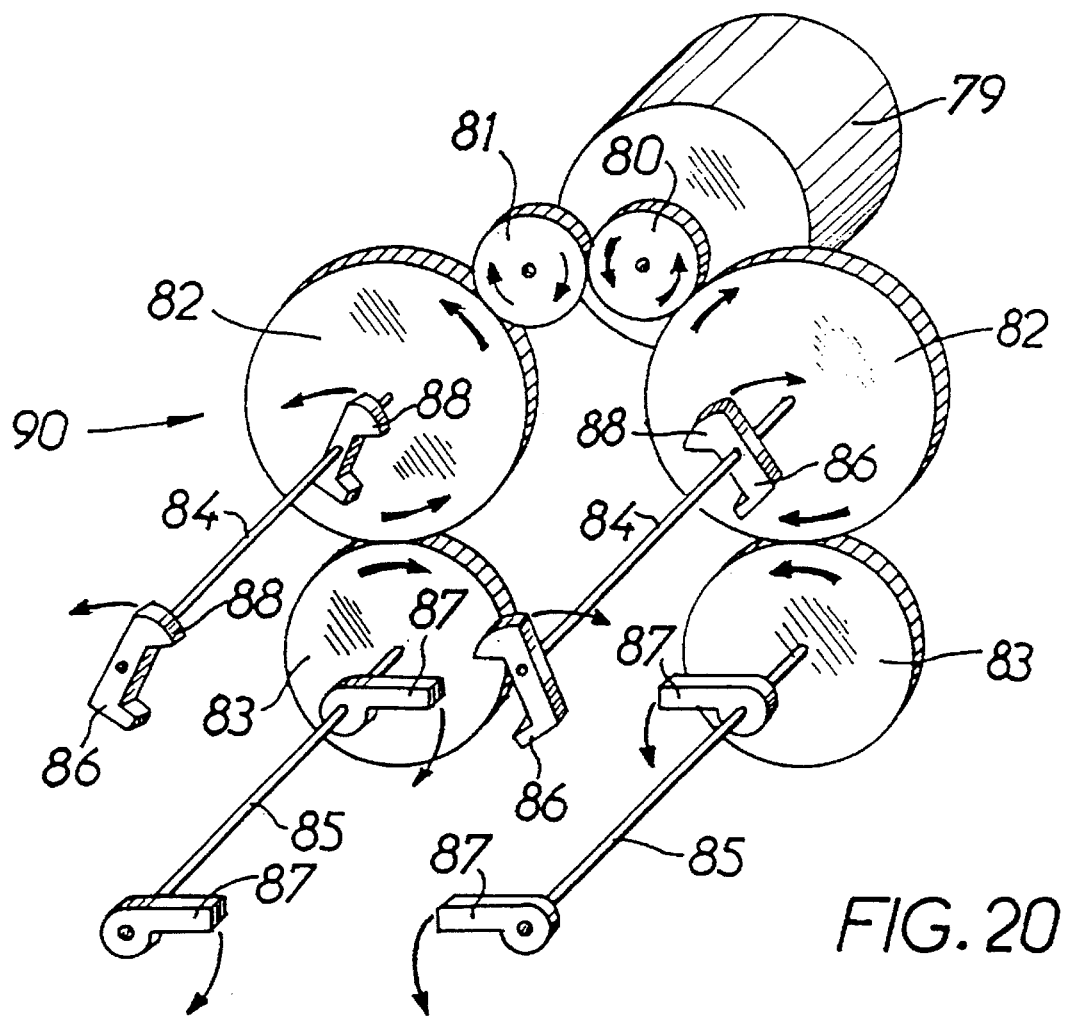
FIG. 20 is a perspective view of the mechanism with retractable stops of the present invention.
Figure 23:
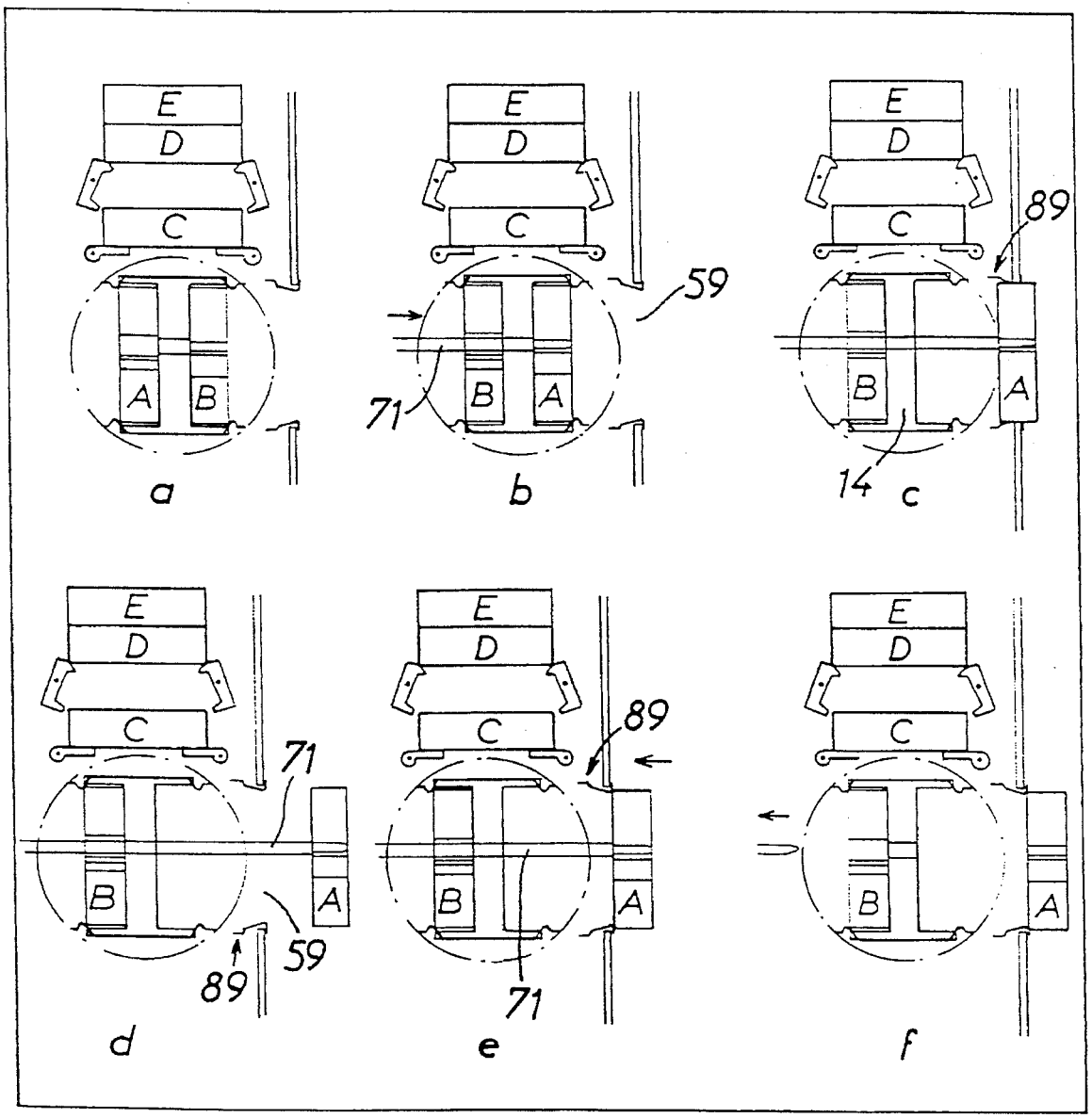

The four bottom stops 87 support a cassette when they are in the horizontal position, as shown in FIG. 20, or release it when they are in the vertical position and open the clips 25 of rotary carriage 14. It will be noted that the horizontal position of the bottom stops 87 corresponds to a position of the top stops 86, the upper tips of which are inclined inwards (FIG. 20). Conversely, motor 79, through the action of the drive pinions, can change the inclination of the top stops at the same time as the bottom stops move into vertical position.

FIG. 21 illustrates the main stages of loading the first two cassettes into rotary carriage 14.

At the start of the operation (FIG. 21a), cassettes A, B, C ... are in cavity 1 of the analyzer and bearing on the upper tips of the top stops 86. The bottom stops 87 are horizontal and do not for the time being, play any part. The motor then actuates the retractable stops, which adopt a reverse position (FIG. 21b). Cassette A then drops and comes to rest on the lower tips of the top stops 88. Further reversal of the stops, illustrated by the arrows (FIG. 21c) will release cassette A, which will move down to the bottom stops 87. At the same time, the upper tips of the top stops 86 will have returned to their initial positions and then support cassette B. The device is then in the position illustrated in FIG. 21d. It will be appreciated that a further reversal of the stops (21c) in the direction of the arrows will lead to the clips being opened and to the dropping of cassette A into the rotary carriage, but it will also release cassette B, which will move down to bear on the lower tips of the top stops. It can be seen that, at each reversal of the positions of the stops, a cassette will move down one step. FIG. 21f illustrates the final result of this first loading stage, wherein the first cassette, A, is in place in the rotary carriage, held by the clips, whereas the second cassette, B, is in waiting position on the bottom stops. The carriage can then perform rotations to agitate cassette A. Then, it halts, cassette A being located in the lower position (FIG. 22) and cassette B can then be loaded.

After agitation, the carriage returns to the vertical position represented in FIG. 23a. The tubes of cassette A are then pierced and sampled through the intermediary of the sampling station. Then the rotary carriage performs a rotation of 180°, which causes cassette B to be presented for sampling (FIG. 23b). Cassette A is subsequently ejected with the help of ejectors 71, which are moved, for this purpose, from left to right (FIG. 23c) and disengage cassette A in the direction of the reception bin through opening 59. It will be noted that the opening is bordered by non-return clips 89. The movement is continued beyond the opening (FIG. 23d), and then the ejectors reverse until cassette A comes to bear against the non-return clips (arrow in FIG. 23e). The ejectors then withdraw to the left (FIG. 23f). The loading and sampling cycle can then be continued.

The sampling station used with this alternative form of embodiment is identical with that of the first variant and has been described with reference to FIG. 7. The alternative embodiment represented in FIGS. 12 to 20 has, in particular, the advantage of taking up little space, and of using a smaller number of parts, which contributes to a reduction in the cost of the apparatus.

Figure 24:
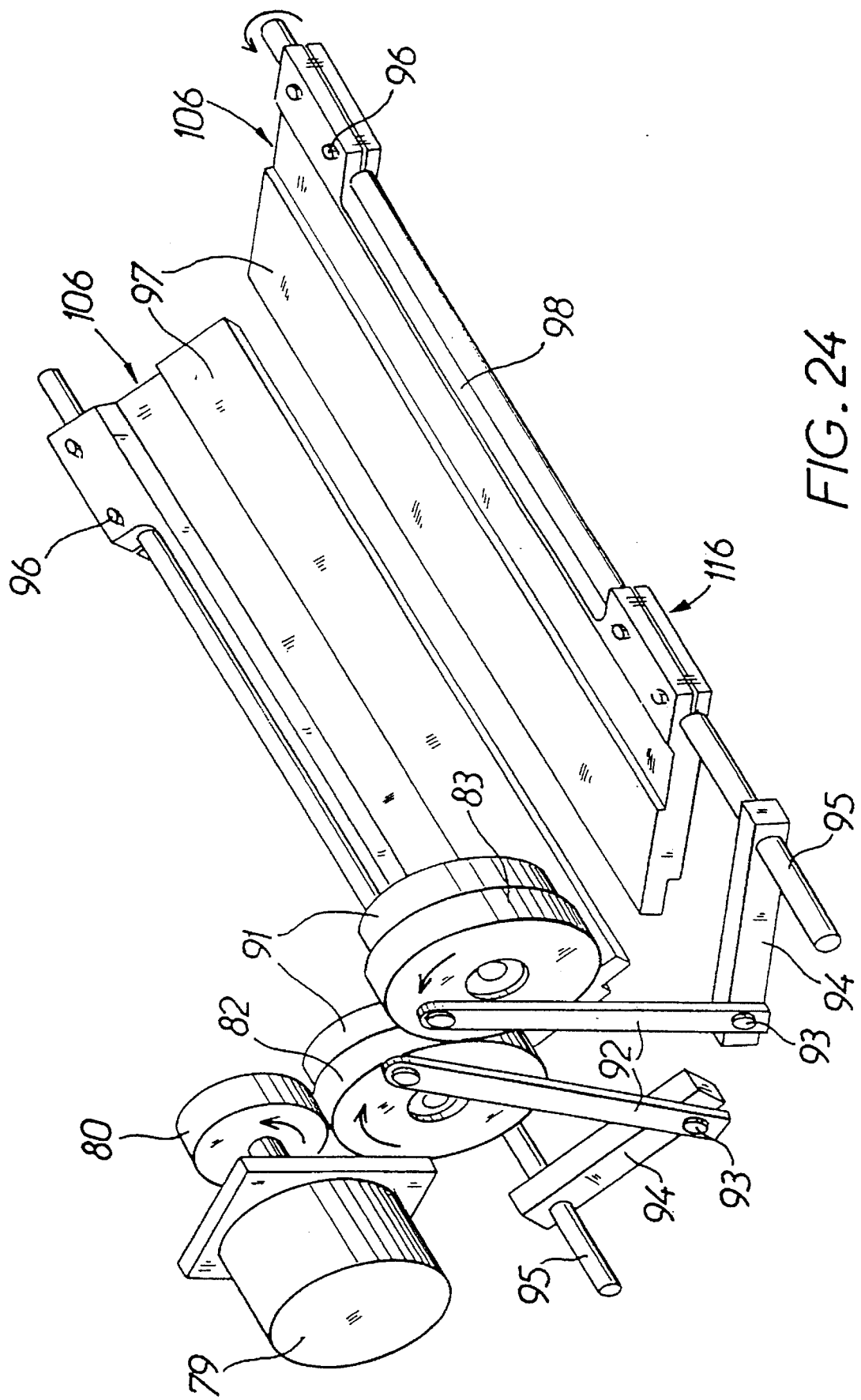
FIGS. 24 and 25 are perspective views of an alternative embodiment of the loading mechanism of the present invention.

Another alternative form of embodiment of a loading mechanism, 116, is now described with reference to FIGS. 24 and 25. It differs from the mechanism illustrated in FIGS. 20 to 23 in the following respects:

The single drive motor 79 drives, via drive pinion 80, two idle pinions (82, 83), each of which carries a cam 91. To each idle pinion is eccentrically fixed a rod 92 articulated via a pivot 93 on a lever 94, the opposite end of which is integral with a lower horizontal pin 94 extending over the entire length of the cassette cavity. By means of lock screws 96, a flap 97 is fixed to pin 95. In its central portion, the flap has a space 98 between it and the pin. It will be noted that the upper face of the said flap is hollowed so as to provide, on a portion of its surface, a longitudinal groove 106.

Figure 25:
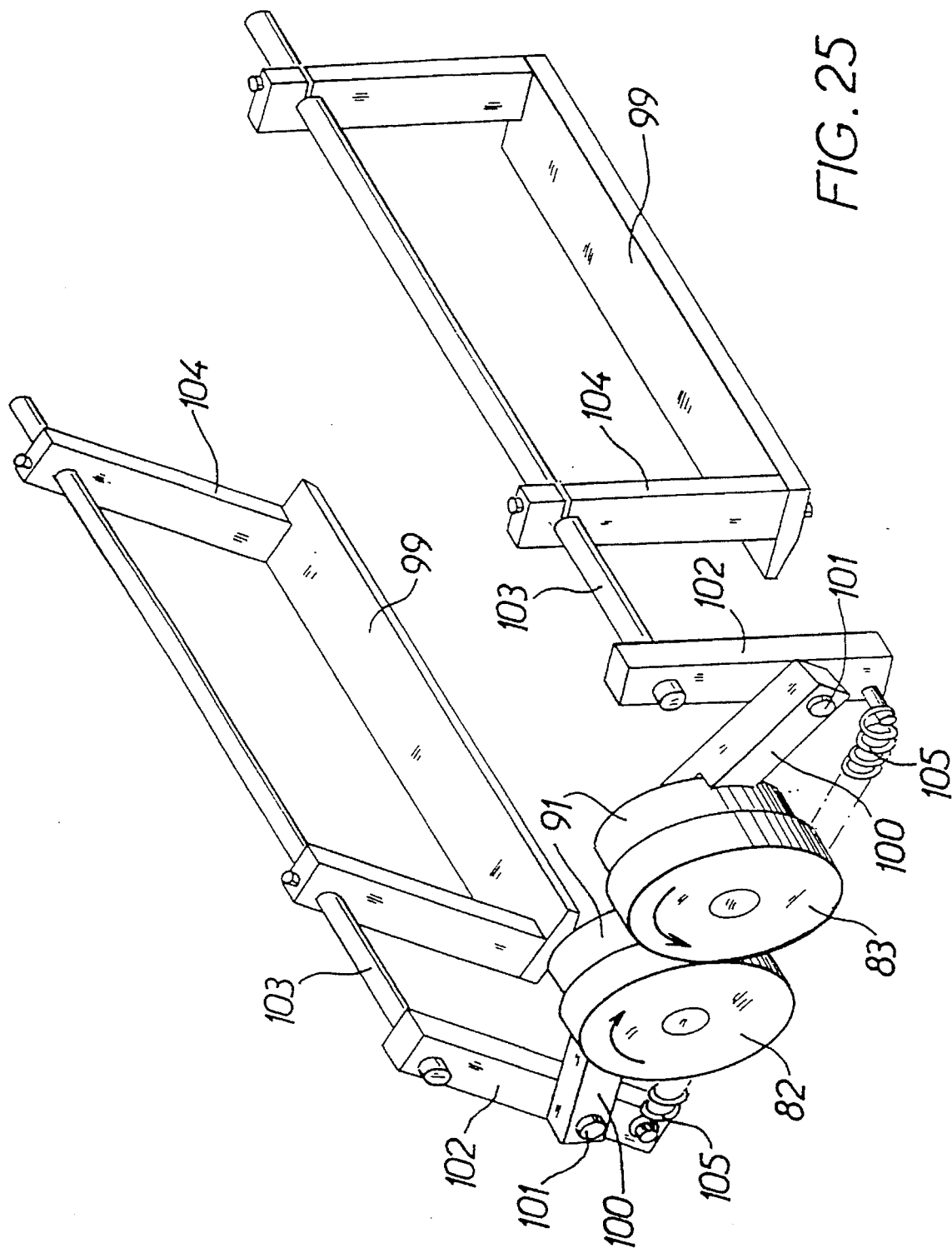

Furthermore, as can be seen more clearly from FIG. 25, each cam 91 acts upon a pivoting member 99 via a cam lever 100 held by its end on the pin of the corresponding idle pinion (82, 83). The opposite end of cam lever 100 is articulated via a pivot 101 on a return lever 102, the opposite end of which is integral with an upper horizontal pin 103, also extending over the entire length of the cassette cavity. By means of brackets 104, pin 103 carries pivoting member 99 taking the form of a substantially horizontal plate located in the area of space 98. The lower portion of return lever 102 is biased by a spring 105.

The different parts previously described are symmetrical on either side of a vertical median plane located between the two idle pinions. It will be appreciated that motor 79 thus acts simultaneously upon the two side flaps 97 and upon the two members 105, to cause them to tilt.

The different stages involved in loading the cassettes into the rotary carriage are illustrated in FIGS. 26 to 30.

Figure 26:
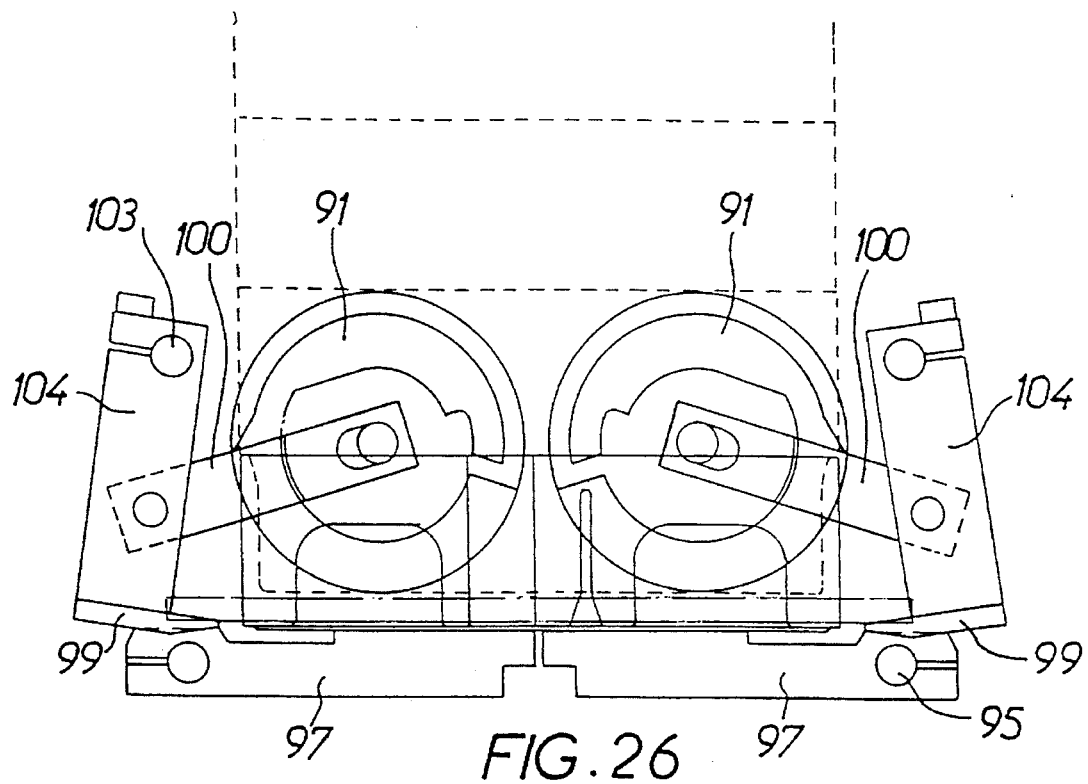
FIGS. 26 to 30 are elevation views of this variant of the loading mechanism during the various loading-unloading stages.
Figure 27:
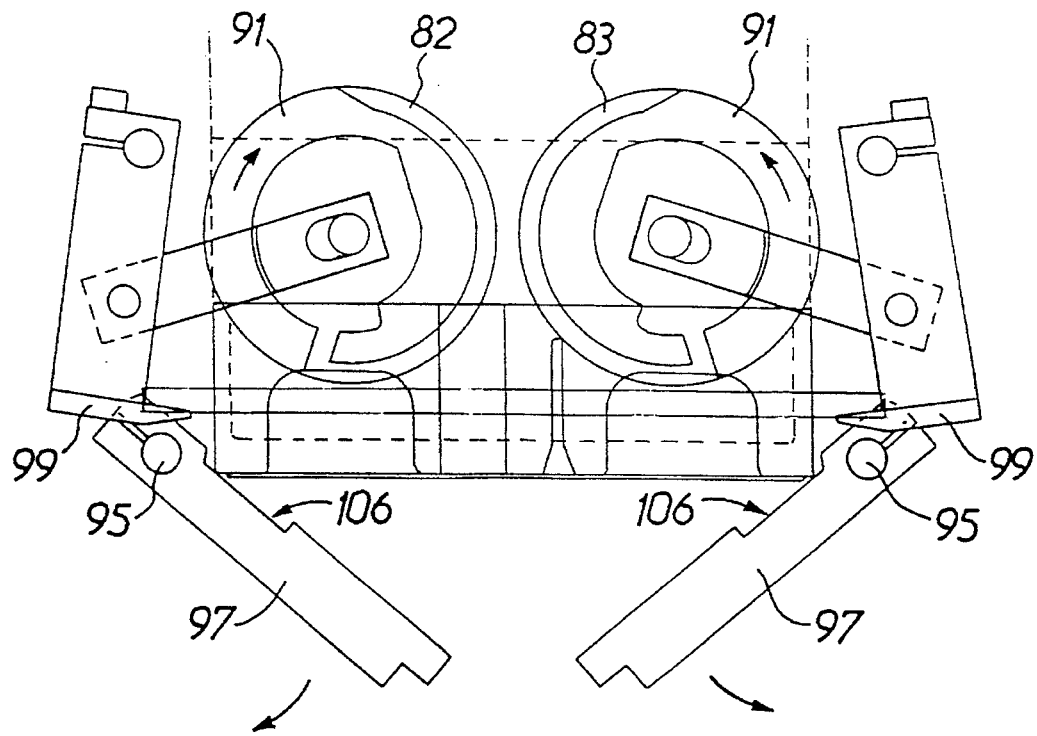
Figure 28:
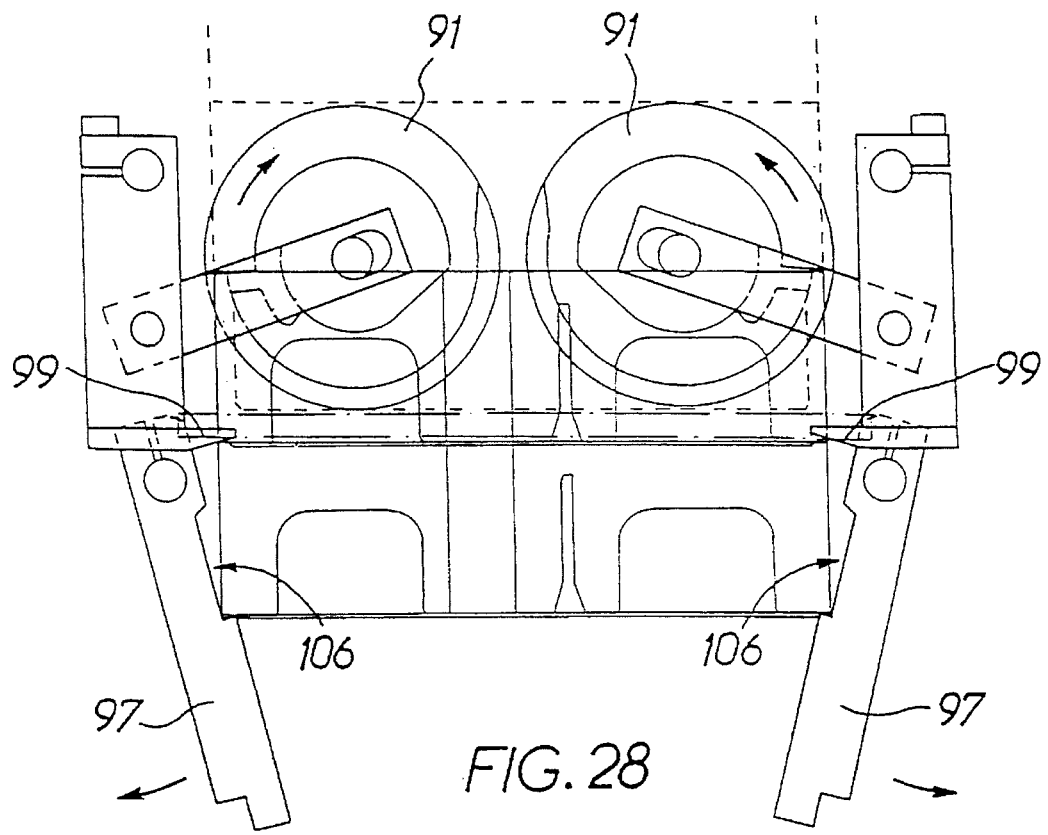
Figure 30:
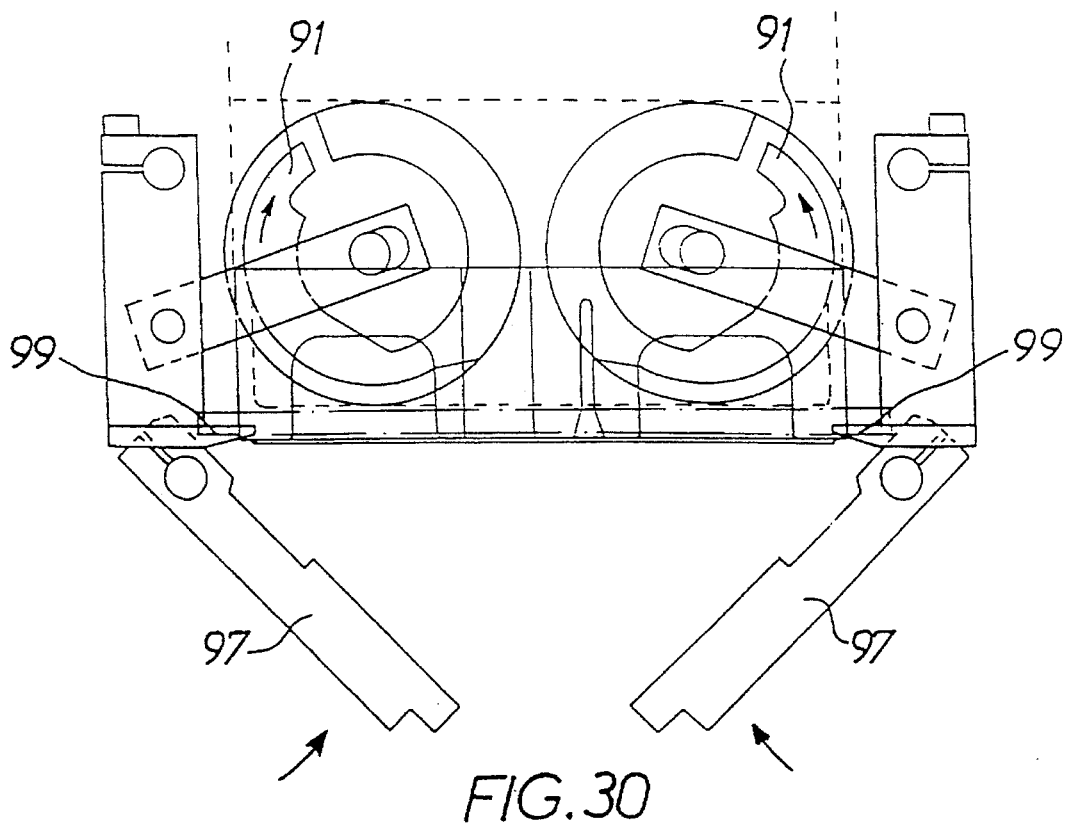

FIG. 26 illustrates the rest position of the mechanism. Flaps 97 are in horizontal position. On the other hand, members 99 are spaced in open position, brackets 104 being slightly inclined owing to the positions of cam levers 100 controlled by cams 91. The pile of cassettes stacked in the cavity thus rests on the horizontal flaps 97.

In the following stage (FIG. 27), the motor has driven the idle pinions (82, 83) in rotation in opposite directions, as indicated by the arrows.

Via rods 92 and levers 94 (not shown in FIG. 27), the lower pins 95 will pivot and flaps 97 will open downwards. During this stage, the profiles of cams 91 is such that members 99 remain disengaged, as in the initial stage. The stack of cassettes has thus begun to slide down into the bottom of the grooves 106 provided in the flaps.

The opening movement of flaps 97 continues (FIG. 28) and the stack of cassettes is then halted on the edges of the grooves 106 provided on the flaps. At the same time, cams 91 have caused the swift closure of members 99, which pass through spaces 98 to lock the preceding cassette and immobilize the stack.

Figure 29:
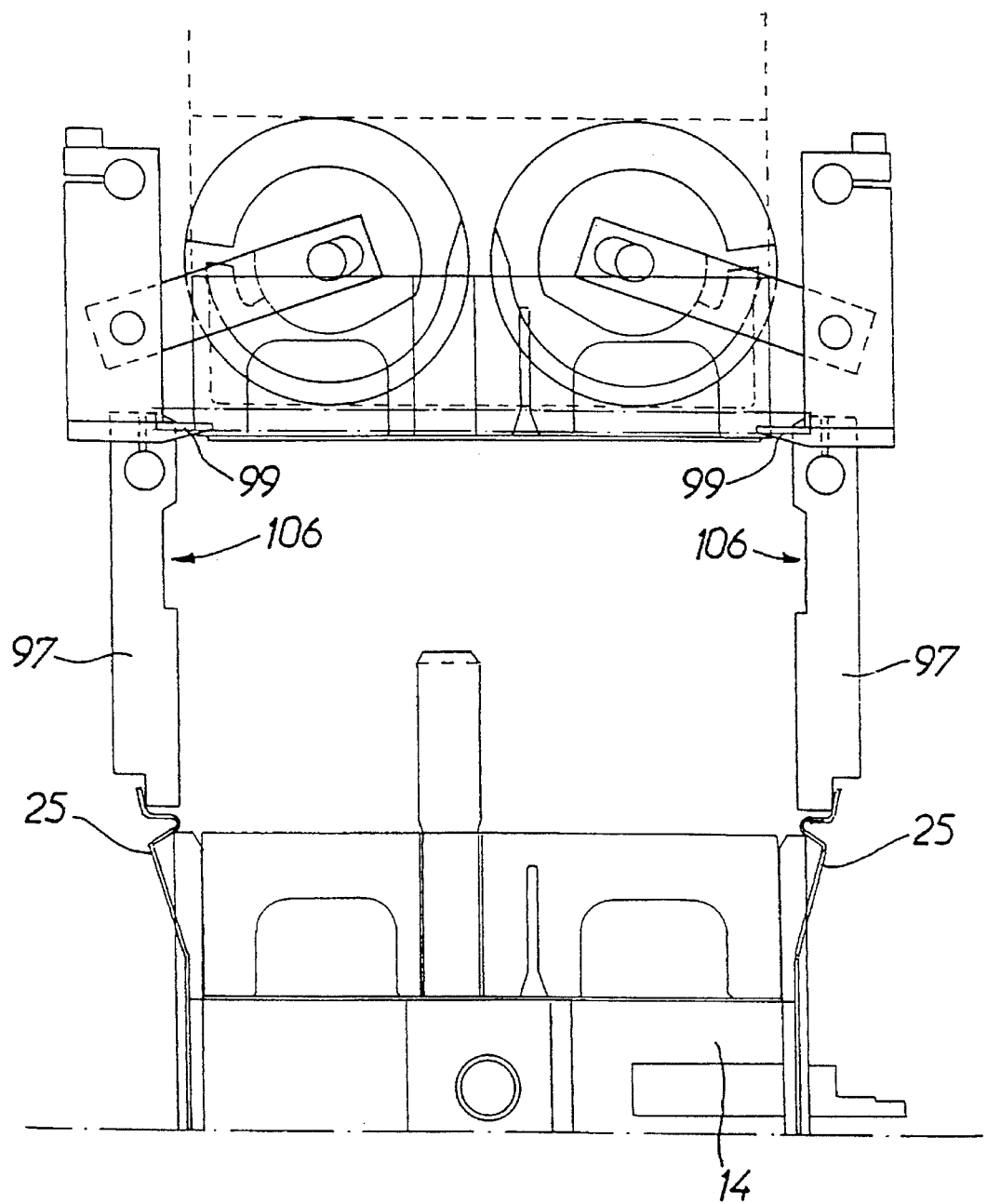

FIG. 29 illustrates the end of the opening movement of flaps 97, which are in the vertical position. The first cassette has escaped from the grooves 106 and can drop into the cavity in rotary carriage 14. Members 99 are still closed and lock the stack above the cassette in the process of being loaded. The ends of flaps 97 in the final opening stage have opened clips 25 with which the rotary carriage is equipped, and the cassette can thus enter the cavity of the carriage.

Following loading of this cassette, flaps 97 move up again (FIG. 30), while members 99 remain in locking position. We then return to the initial position of FIG. 26, and the loading cycle can continue.

One advantage of this rod and cam type device is that the closing and opening cycle is effected by rotation in the same direction, full circle, of the idle pinions, which makes it possible to have a cam profile that is different when the flaps move down (first half-circle) from that when they move up again (second half-circle). This permits a smooth descent of the stack by the height of a cassette, before this stack is locked, and then a progressive dropping of the cassette which slides along the flaps and, finally, when the latter move up again, the opening of members 99 at the last moment, so that the stack bears on the flaps without any sudden movements.

Figure 31:
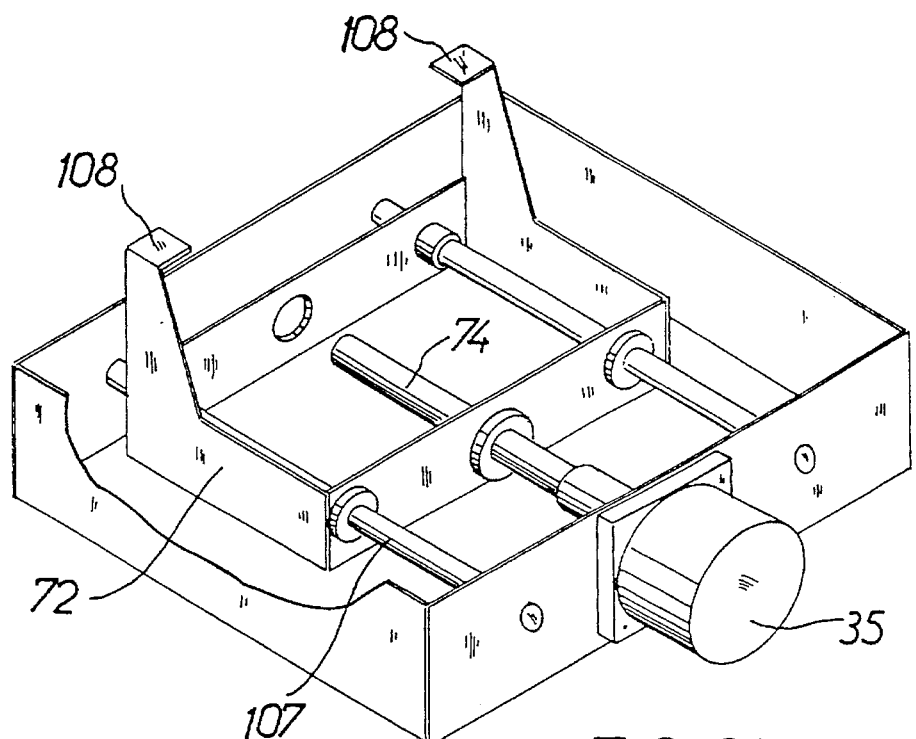
FIG. 31 is a perspective view of another alternative embodiment of the ejection mechanism of the present invention.

The mechanism that enables a cassette to be ejected from the rotary carriage, according to another alternative embodiment, is represented in FIG. 31, which bears certain reference numbers that are identical with those of FIG. 17, to denote the same elements. The mechanism of FIG. 31 differs therefrom, not in terms of its principle but in terms of assembly. The figure shows a mobile drawer member 72 which is driven by a rotating screw 74 driven by a motor 35, and which slides on guide pins 107. On its upper portion, the mobile drawer member has two horizontal tabs 108 designed to engage with a cassette ready to be discharged from the rotary carriage. For this purpose, the cassettes are provided with slots with entry slopes via which the said tabs penetrate in the ejection stage.

Figure 32:
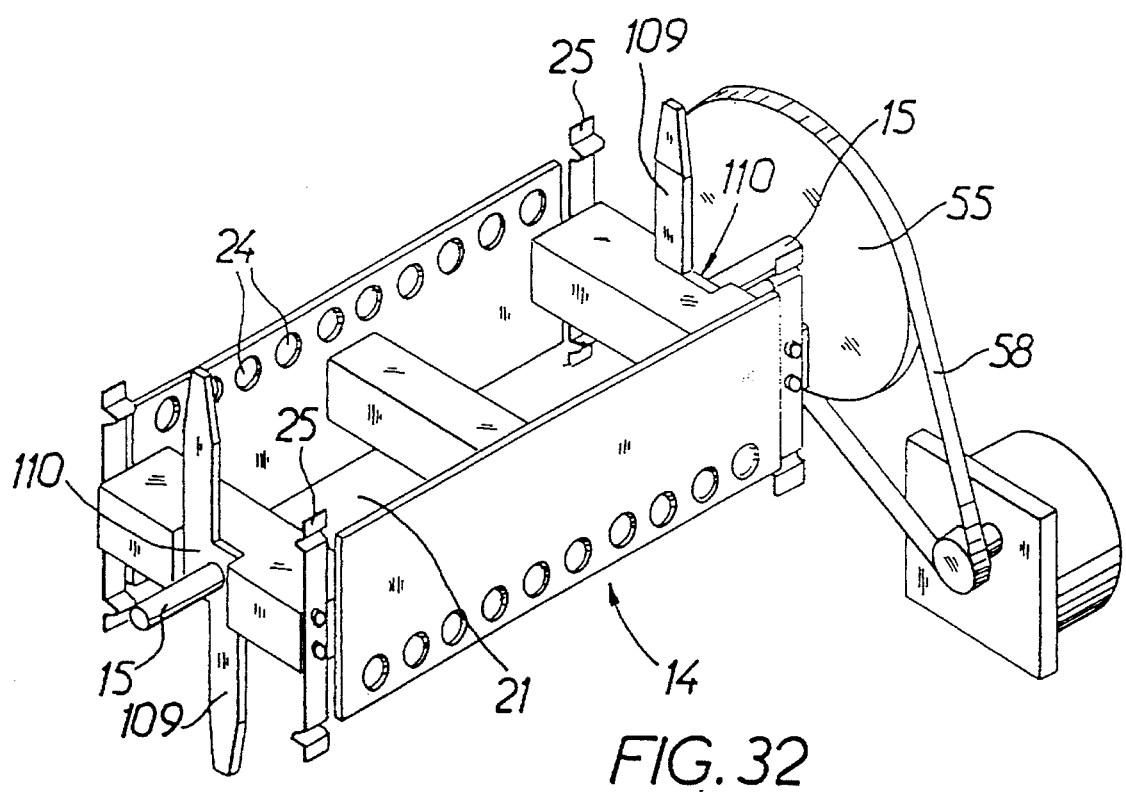
FIG. 32 is a perspective view of another alternative embodiment of the rotary carriage of the present invention.

A variant of the rotary carriage adapted to this variant of the loading mechanism is illustrated in FIG. 32. The same elements as those in FIG. 18 bear the same reference numbers. To rotary carriage 14 have been added cassette guides 109, which take the form of strips mounted on the ends of each cradle 21 and the purpose of which is to guide the cassette as it moves down into the cavity, at the same time as they hold it in position longitudinally. Guides 109 are mounted asymmetrically on either side of rotary shaft 15. About this shaft, a clear space 110 is provided at the two ends of the carriage which allows tabs 108 of the ejection mechanism to be parked when the carriage is rotating.

Figure 7:
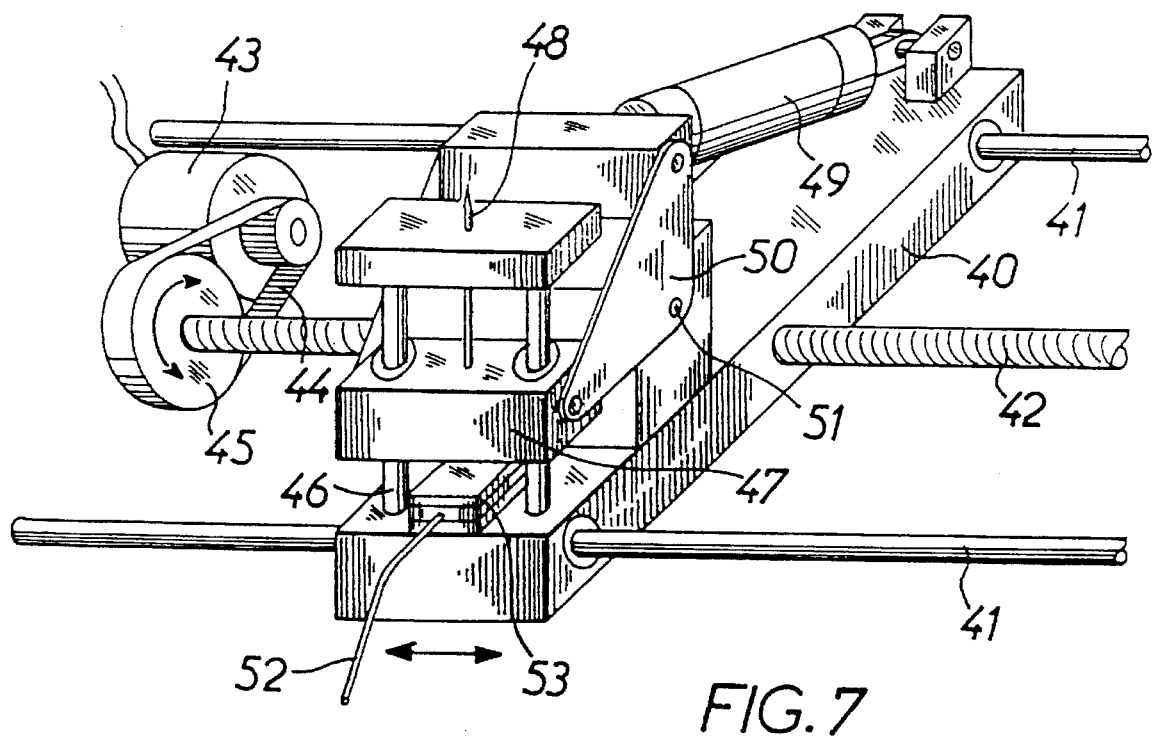
FIG. 7 is a perspective view of the mobile piercing device of the present invention.
Figure 33:
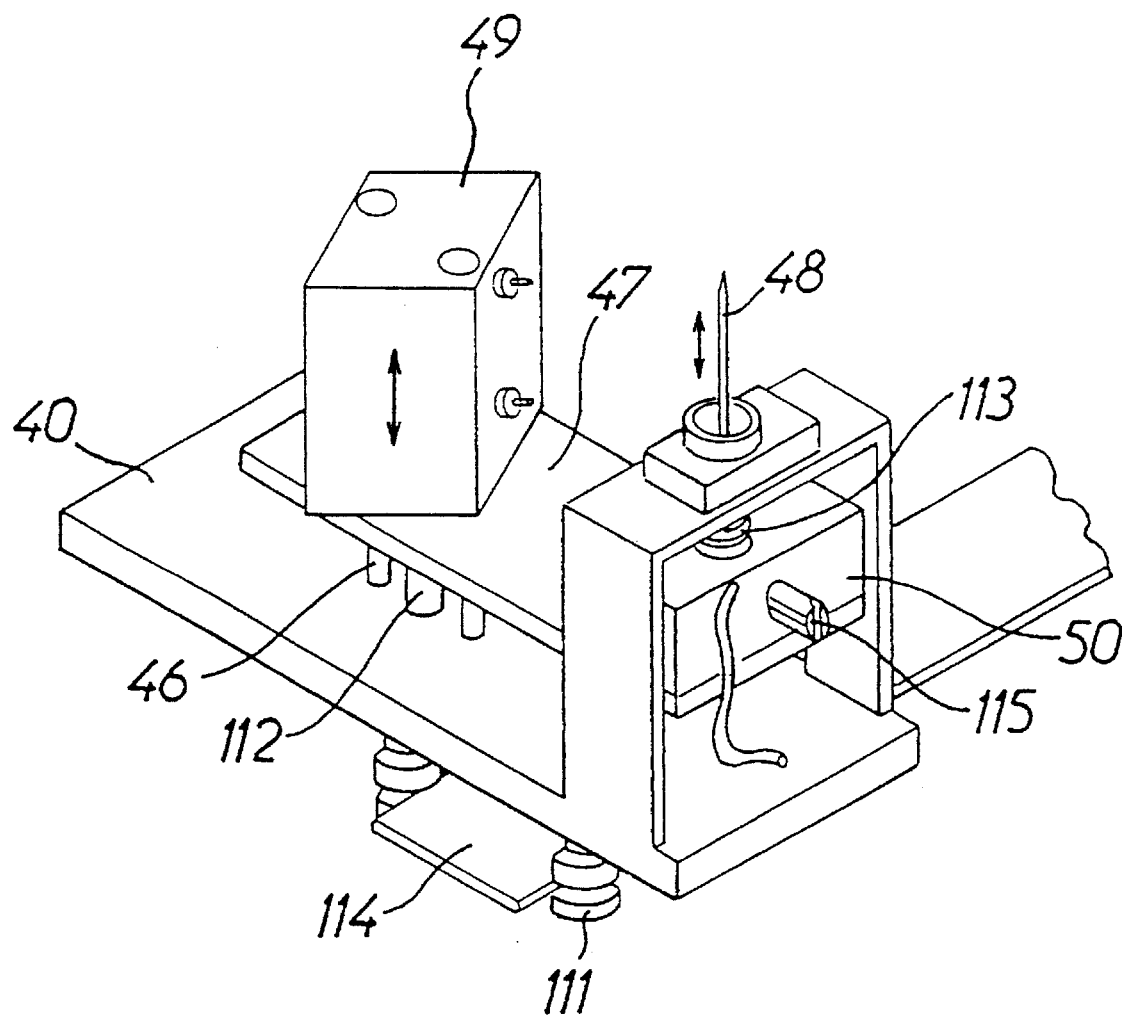
FIG. 33 is a perspective view of another alternative embodiment of the mobile piercing device of the present invention.

FIG. 33 shows an alternative embodiment of the piercing device of FIG. 7. Base 40 is mounted on guide rollers 111 cooperating with a rail 114. Through plate 47 mounted on its guide columns 48 passes a pin 112 bearing a jack 49 of the dual effect anti-rotation type. The plate is fixed rigidly to the jack. The vertical sampling needle 48 is mounted on a block 50 integral with the plate. Bellows 113 ensure the tightness of the needle, held in place by a locking piece 115.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A device for transferring, agitating, and sampling blood products sealed in tubes by pierceable bungs, wherein said tubes are grouped together in cassettes, comprising:

storage means for holding one or more cassettes of tubes sealed by pierceable bungs;

means for extracting a cassette from said storage means and transferring said cassette to, and positioning said cassette in a rotary carriage means;

rotary carriage means for rotating said tubes and thereby mixing their contents and for temporarily immobilizing said tubes in an inverted vertical position for sampling, comprising two U-shaped cradles for receiving and holding said cassettes, wherein said U-shaped cradles are symmetrical to, disposed on, and opening outward from, a rotatable shaft;

sampling means for removing one or more samples of said blood products from said tubes;

means for ejecting said cassette from said cradles; and a reception bin for receiving cassettes ejected from said cradles.

2. The device according to claim 1, wherein said storage means comprises a tray provided with a vertical rear face having a lower portion with a transverse aperture, and side walls, one of which is pierced at one end of the transverse aperture by an opening to permit the passage of said cassette, and by an analogous opening in an upper portion of said sidewall.

3. The device according to claim 1 wherein said rotary carriage means further comprises a central body provided at a bottom of said cradles and further comprises clips for locking said cassettes into said cradles.

4. The device according to claim 1, wherein said cradles each further comprises two sides, one of which comprises a slot, the other of which is pierced by a plurality of orifices corresponding to the number of tubes in said cassette.

5. The device according to claim 1 wherein said rotary carriage means further comprises cassette guides mounted at a top of each cradle on either side of the rotational shaft and providing a clear space.

6. The device according to claim 3, wherein said central body further comprises a disengagement groove between the cradles symmetrically in relation to the shaft.

7. The device according to claim 1, wherein said rotary carriage means further comprises a drive pulley pierced by two rectangular openings designed to permit the passage of said cassettes when ejected by said ejection means from said cradles.

8. The device according to claim 1, wherein said means for extracting a cassette from said storage means and transferring said cassette to, and positioning said cassette in, said rotary storage means, and said means for ejecting said cassette from said cradles, comprise a single loading and ejection carriage which moves from said storage means to said rotary carriage means, and vice versa, by sliding along a linear guide member parallel to said rotatable shaft of said rotary carriage means.

9. The device according to claim 8, wherein said loading and ejection carriage comprises a fixed pin mounted on said loading and ejecting carriage and extending in the direction of said rotatable shaft of said rotary carriage means.

10. The device according to claim 9, further comprising a jack ensuring maneuvering of a retractable loading finger travelling perpendicularly to said rotatable shaft.

11. The device according to claim 10, wherein said fixed pin is mounted on a bracket integral with said loading and ejecting carriage, and wherein said bracket is pierced by an orifice to permit the passage of a retractable loading finger.

12. The device according to claim 8, wherein said linear guide member comprises ball bearing-mounted rods, and wherein said loading and ejection carriage is driven by an endless serrated belt driven by a motor.

13. The device according to claim 3, further comprising means for ensuring the proper positioning of said cassette in said rotary carriage means by opening said clips comprising a plurality of retractable stops which are driven to tilt by the action of a single motor thereby retaining or releasing said cassettes into said rotary carriage means through the effect of gravity.

14. The device according to claim 13, wherein said retractable stops comprise a plurality of top stops mounted at the same height on top pins, and a plurality of bottom stops mounted at the same height, which is lower than the height of said top stops, on bottom pins, wherein said pins are driven in rotation simultaneously.

15. The device according to claim 14, wherein said top pins and bottom pins extend outwards respectively from two top and bottom pinions driven by said single motor via a drive pinion and a reversing pinion.

16. The device according to claim 14, wherein said top stops comprise a catch symmetrical in relation to its axis of rotation, and having tips oriented inwards in the direction of the adjacent top pin.

17. The device according to claim 14, wherein said bottom stops are asymmetrical in relation to said bottom pins and oriented inwards in the direction of the adjacent bottom pins.

18. The device according to claim 3, further comprising means for ensuring the positioning of said cassette in a cavity in said rotary carriage means comprising two flaps and two members which are driven to tilt by the action of a single motor to thereby retain a stack of said cassettes and/or to release a cassette into said rotary carriage means.

19. The device according to claim 18, wherein said single motor drives two idle pinions each carrying a rod acting on a flap and a cam acting on a pivoting member.

20. The device according to claim 19, wherein said rod is articulated on a lever, the end of which is integral with a lower horizontal pin extending over the entire length of said cavity, and wherein said flap is fixed on said pin.

21. The device according to claim 20, wherein said flap comprises an upper face that is hollowed so as to provide on a portion of its surface a longitudinal groove.

22. The device according to claim 19, wherein said cam controls a cam lever articulated on a return lever integral with an upper horizontal pin extending over the entire length of said cavity, and wherein said pivoting member is fixed on said pin.

23. The device according to claim 1, wherein said sampling means comprises a vertical sampling needle, having an upwardly oriented tip and displaceable vertically by sliding over guide columns under the action of a jack, mounted on a mobile base of a sampling station, wherein said mobile base also supports another micro-sampling needle oriented downwards.

24. The device according to claim 1, wherein said sampling means comprises a vertical sampling needle, having an upwardly oriented tip and which is vertically displaceable mounted on a plate through which passes a pin bearing a jack wherein said plate is rigidly fixed to said jack.

25. The device according to claim 23, wherein said sampling station is disposed near a fixed support of a tube intended for priority sampling, and is capable of reading a bar code that is disposed on the sampled tube.

26. The device according to claim 1, wherein said means for ejecting said cassette from said cradles comprises two ejectors sliding in a fixed guide block, wherein said ejectors comprise heads which pass through openings in said rotary carriage means to push the cassette out of said cradles.

27. The device according to claim 26, wherein said sliding ejectors are displaced by a rotating screw driven by a motor integral with a guide block.

28. The device according to claim 1, wherein said means for ejecting said cassette out of said cradles comprises a mobile drawer member bearing two tabs for engaging with said cassette.

29. The device according to claim 1, further comprising a pusher means for disengaging the cassettes in the direction of a collecting tray placed flat in said reception bin.

* * * * *